United States Patent [19]
Cary et al.

[11] Patent Number: 5,516,918
[45] Date of Patent: May 14, 1996

[54] SUBSTITUTED BENZOPYRAN AND TETRAHYDRONAPHTHALENE COMPOUNDS USEFUL FOR SAFENING HERBICIDES IN CROPS

[75] Inventors: Gail E. Cary, Lawrenceville; Nina R. Quinn, Stockton, both of N.J.

[73] Assignee: American Cyanamid Company, Madison, N.J.

[21] Appl. No.: 381,673

[22] Filed: Jan. 31, 1995

Related U.S. Application Data

[62] Division of Ser. No. 25,545, Mar. 3, 1993, Pat. No. 5,407,897.

[51] Int. Cl.⁶ .................... C07D 335/04; C07D 307/34; C07D 407/00; C07D 311/74
[52] U.S. Cl. ............. 549/23; 549/252; 549/370; 549/405; 504/288; 504/292; 504/293
[58] Field of Search ............... 549/23, 252, 370, 549/405; 504/288, 292, 293

[56] References Cited

U.S. PATENT DOCUMENTS

| | | | |
|---|---|---|---|
| 4,210,663 | 7/1980 | Belletire | 424/275 |
| 4,307,108 | 12/1981 | Belletire et al. | 424/274 |
| 4,347,372 | 8/1982 | Föry et al. | 548/217 |
| 4,442,114 | 4/1984 | Belletire et al. | 424/267 |
| 4,471,124 | 9/1984 | Belletire et al. | 548/410 |
| 4,503,066 | 3/1985 | Brittain et al. | 514/409 |
| 4,992,092 | 2/1991 | Birk et al. | 504/103 |
| 5,039,672 | 8/1991 | Eggler et al. | 514/210 |

FOREIGN PATENT DOCUMENTS

| | | |
|---|---|---|
| 0012158 | 6/1980 | European Pat. Off. . |
| 0065392 | 11/1982 | European Pat. Off. . |

OTHER PUBLICATIONS

C. Lipinski et al., Journal of Medicinal Chemistry, 35, pp. 2169–2177 (1992).
L. Rice et al., Journal of Heterocyclic Chemistry, 8, pp. 155–156 (1971).
B. Mylari et al., Journal of Medicinal Chemistry, 34, pp. 1011–1018 (1991).
R. Sarges et al., Journal of Medicinal Chemistry, 31, pp. 230–243 (1988).
Mylari et al., "A Highly Specific Aldose Reductase Inhibitor, Ethyl 1–Benzyl–3—Hydroxy–2 (5H)–oxopyrrole–4–carboxylate and Its Congeners," J. Med. Chem. 34(3): 1011–18 (1991).
Rice et al., "Spirans XVII. Spirans Derived from 4–Chromanone (1)," J. Heterocyclic Chemistry 8(1):155–56 (Feb. 1971).

Primary Examiner—Allen J. Robinson
Assistant Examiner—Mary C. Cebulak
Attorney, Agent, or Firm—Peggy A. Climenson

[57] ABSTRACT

There is provided a method for safening herbicides in crop plants by using substituted benzopyran or tetrahydronaphthalene compounds of formula I

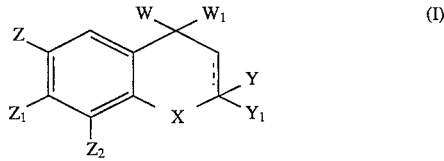

Further provided are compounds of formula II and compositions comprising a herbicide and an antidotally effective amount of a substituted benzopyran or tetrahydronaphthalene compound of formula I.

4 Claims, No Drawings

SUBSTITUTED BENZOPYRAN AND TETRAHYDRONAPHTHALENE COMPOUNDS USEFUL FOR SAFENING HERBICIDES IN CROPS

This is a divisional of application Ser. No. 08/025,545 filed on Mar. 3, 1993, now U.S. Pat. No. 5,407,897.

BACKGROUND OF THE INVENTION

One of the most common practices for controlling undesirable plant species is the use of herbicides. However, it is known that when certain herbicides are applied in effective amounts they may also damage the crop plants. For example, certain herbicides which are effective against certain annual and perennial grass weeds cannot be used in all crops, especially cereal crops such as corn, sorghum, oat, wheat, barley and rice because the herbicide injures the crops as well as controls the weeds.

It is therefore an object of the present invention to provide a method for protecting crops from injury caused by an herbicide which comprises applying to the crop plant, the seed of the crop, or the soil or water surrounding the crop or crop seed an effective antidotal amount of a substituted benzopyran or tetrahydronaphthalene compound.

It is also an object of the present invention to provide a safened herbicidal composition comprising a herbicide and a substituted benzopyran or tetrahydronaphthalene compound.

It is a further object of this invention to provide compounds useful as safeners.

These and other objects of the present invention will become more apparent from the detailed description thereof set forth below.

SUMMARY OF THE INVENTION

The present invention relates to a method for protecting crops from injury caused by a herbicidally effective amount of a herbicide by applying to the crop plant, the seed of the crop, or the soil or water surrounding the crop or crop seed an effective antidotal amount of a substituted benzopyran or tetrahydronaphthalene compound of formula I

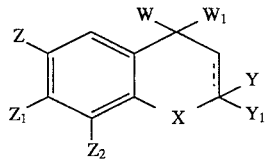

(I)

wherein
X is O, $S(O)_q$ or $CH_2$;
q is an integer of 0, 1 or 2;
Z, $Z_1$ and $Z_2$ are each independently hydrogen, halogen, $C_3$–$C_{10}$ alkenyl, $C_3$–$C_{10}$ alkynyl, furfuryl, $C_1$–$C_7$ alkoxy, $C_3$–$C_{10}$ alkenyloxy, $Z_3C(O)$, $Z_4S(O)_p$, $C_1$–$C_{10}$ alkyl optionally substituted with one or more halogen atoms, hydroxy groups, amino groups, thio groups, $C_1$–$C_5$ alkylcarbonyl groups or $C_1$–$C_5$ alkoxy groups, or phenoxy optionally substituted with one or more halogen atoms or $C_1$–$C_4$ alkyl groups optionally substituted with one or more halogen atoms;
$Z_3$ is $C_1$–$C_6$ alkyl;
$Z_4$ is $C_1$–$C_6$ alkyl;
p is an integer of 0, 1 or 2;

Y and $Y_1$ are each independently hydrogen, $C_1$–$C_6$ alkyl, halogen, phenyl, $C_1$–$C_6$ alkoxy, amino or $C_1$–$C_6$ alkylcarbonyl;
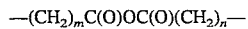 represents a single or double bond with the proviso that when 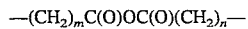 represents a double bond then $Y_1$ is not present;
W and $W_1$ are each independently $(CRR_1)_rA$, and when taken together with the carbon atom to which they are attached W and $W_1$ may form a ring in which $WW_1$ is represented by the structure:

—$(CH_2)_m C(O)OC(O)(CH_2)_n$— with the proviso that when n is 1 then m is 1;
n is an integer of 0 or 1;
m is an integer of 1 or 2;
r is an integer of 0, 1, 2 or 3;
R is hydrogen, $C_1$–$C_{10}$ alkyl, $C_3$–$C_6$ alkenyl, $C_3$–$C_6$ alkynyl, $C_3$–$C_6$ cycloalkyl or $C_1$–$C_{10}$ alkoxy;
$R_1$ is hydrogen or $C_1$–$C_{10}$ alkyl;
A is $C(O)X_1$, $C(S)OR_2$, $CR_3(OR_4)_2$ or cyano;
$X_1$ is $OR_5$, $R_6$, $NR_7R_8$ or $SR_9$;
$R_2$, $R_5$ and $R_9$ are each independently hydrogen, $C_3$–$C_{10}$ alkenyl, $C_3$–$C_{10}$ alkynyl, furfuryl, $C_1$–$C_{10}$ alkyl optionally substituted with one or more halogen atoms, or an alkali metal, alkaline earth metal, manganese, copper, zinc, cobalt, silver, nickel, ammonium or organic ammonium cation;
$R_3$ and $R_6$ are each independently hydrogen or $C_1$–$C_{10}$ alkyl optionally substituted with one or more halogen atoms;
$R_7$ and $R_8$ are each independently hydrogen, $C_3$–$C_{10}$ alkenyl or $C_1$–$C_{10}$ alkyl;
$R_4$ is $C_3$–$C_{10}$ alkenyl, $C_3$–$C_{10}$ alkynyl or $C_1$–$C_{10}$ alkyl and when taken together $R_4$ and a second $R_4$ may form a ring which $R_4R_4$ are represented by —$(CH_2)_2$— or —$(CH_2)_3$—; and the optical isomers thereof.

The invention also relates to compounds which are useful for safening important agricultural crops against herbicidal injury.

The invention further relates to a safened herbicidal composition which is effective against weeds, but spares the crop.

DETAILED DESCRIPTION OF THE INVENTION

The present invention relates to a method of safening herbicides by applying a chemical safener, a substituted benzopyran or tetrahydronaphthalene compound of formula I, to the seed of the crop, the foliage of the crop or the soil or water surrounding the crop or crop seed.

The safener compounds of the present invention have the following structural formula I

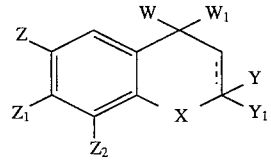

(I)

wherein
X is O, $S(O)_q$ or $CH_2$;

q is an integer of 0, 1 or 2;

Z, $Z_1$ and $Z_2$ are each independently hydrogen, halogen, $C_3$–$C_{10}$ alkenyl, $C_3$–$C_{10}$ alkynyl, furfuryl, $C_1$–$C_7$ alkoxy, $C_3$–$C_{10}$ alkenyloxy, $Z_3C(O)$, $Z_4S(O)_p$, $C_1$–$C_{10}$ alkyl optionally substituted with one or more halogen atoms, hydroxy groups, amino groups, thio groups, $C_1$–$C_5$ alkylcarbonyl groups or $C_1$–$C_5$ alkoxy groups, or phenoxy optionally substituted with one or more halogen atoms or $C_1$–$C_4$ alkyl groups optionally substituted with one or more halogen atoms;

$Z_3$ is $C_1$–$C_6$ alkyl;

$Z_4$ is $C_1$–$C_6$ alkyl;

p is an integer of 0, 1 or 2;

Y and $Y_1$ are each independently hydrogen, $C_1$–$C_6$ alkyl, halogen, phenyl, $C_1$–$C_6$ alkoxy, amino or $C_1$–$C_6$ alkylcarbonyl;

===== represents a single or double bond with the proviso that when ===== represents a double bond then $Y_1$ is not present;

W and $W_1$ are each independently $(CRR_1)_rA$, and when taken together with the carbon atom to which they are attached W and $W_1$ may form a ring in which $WW_1$ is represented by the structure:

—$(CH_2)_mC(O)OC(O)(CH_2)_n$— with the proviso that when n is 1 then m is 1;

n is an integer of 0 or 1;

m is an integer of 1 or 2;

r is an integer of 0, 1, 2 or 3;

R is hydrogen, $C_1$–$C_{10}$ alkyl, $C_3$–$C_6$ alkenyl, $C_3$–$C_6$ alkynyl, $C_3$–$C_6$ cycloalkyl or $C_1$–$C_{10}$ alkoxy;

$R_1$ is hydrogen or $C_1$–$C_{10}$ alkyl;

A is $C(O)X_1$, $C(S)OR_2$, $CR_3(OR_4)_2$ or cyano;

$X_1$ is $OR_5$, $R_6$, $NR_7R_8$ or $SR_9$;

$R_2$, $R_5$ and $R_9$ are each independently hydrogen, $C_3$–$C_{10}$ alkenyl, $C_3$–$C_{10}$ alkynyl, furfuryl, $C_1$–$C_{10}$ alkyl optionally substituted with one or more halogen atoms, or an alkali metal, alkaline earth metal, manganese, copper, zinc, cobalt, silver, nickel, ammonium or organic ammonium cation;

$R_3$ and $R_6$ are each independently hydrogen or $C_1$–$C_{10}$ alkyl optionally substituted with one or more halogen atoms;

$R_7$ and $R_8$ are each independently $C_3$–$C_{10}$ alkenyl or $C_1$–$C_{10}$ alkyl;

$R_4$ is $C_3$–$C_{10}$ alkenyl, $C_3$–$C_{10}$ alkynyl or $C_1$–$C_{10}$ alkyl and when taken together $R_4$ and a second $R_4$ may form a ring which $R_4R_4$ are represented by —$(CH_2)_2$— or —$(CH_2)_3$—; and the optical isomers thereof.

Preferred safener compounds of the present invention are those wherein

X is O, $S(O)_q$ or $CH_2$;

q is an integer of 0, 1 or 2;

Z, $Z_1$ and $Z_2$ are each independently hydrogen, $C_1$–$C_4$ alkoxy, F, Cl, Br, phenoxy optionally substituted with one or more halogen atoms or $C_1$–$C_4$ alkyl groups optionally substituted with one or more halogen atoms, or $C_1$–$C_4$ alkyl optionally substituted with one or more halogen atoms, $C_1$–$C_3$ alkoxy groups or hydroxy groups, provided that at least one of Z—$Z_2$ is hydrogen and further provided that only one of Z—$Z_2$ is phenoxy optionally substituted with one or more halogen atoms or $C_1$–$C_4$ alkyl groups optionally substituted with one or more halogen atoms;

Y and $Y_1$ are each independently hydrogen, $C_1$–$C_3$ alkyl, F or Cl, provided that when $Y_1$ is F or Cl, then Y is hydrogen;

===== represents a single bond;

W is $CH_2A$ or when taken together with $W_1$, $WW_1$ is represented by the structure —$CH_2C(O)OC(O)$—;

$W_1$ is A or when taken together with W, $W_1W$ is represented by the structure —$C(O)OC(O)CH_2$—;

A is $C(O)X_1$ or $CH(OR_4)_2$;

$X_1$ is $OR_5$ or $SR_9$;

$R_5$ is hydrogen, $C_1$–$C_6$ alkyl, $C_3$–$C_6$ alkenyl, $C_3$–$C_6$ alkynyl or an alkali metal, alkaline earth metal, manganese, copper, zinc, cobalt, silver, nickel, ammonium or organic ammonium cation;

$R_9$ is hydrogen, $C_1$–$C_6$ alkyl, $C_3$–$C_6$ alkenyl or $C_3$–$C_6$ alkynyl;

$R_4$ is $C_1$–$C_3$ alkyl and when taken together $R_4$ and a second $R_4$ may form a ring in which $R_4R_4$ are represented by —$(CH_2)_2$— or —$(CH_2)_3$—; and the optical isomers thereof.

More preferred safener compounds of the present invention are those wherein

X is O, S or $CH_2$;

Z, $Z_1$ and $Z_2$ are each independently hydrogen, $C_1$–$C_4$ alkoxy, F, Cl, Br, $C_1$–$C_4$ alkyl or phenoxy optionally substituted with one or more halogen atoms or $C_1$–$C_4$ alkyl groups optionally substituted with one or more halogen atoms, provided that at least one of Z—$Z_2$ is hydrogen and further provided that only one of Z—$Z_2$ is phenoxy optionally substituted with one or more halogen atoms or $C_1$–$C_4$ alkyl groups optionally substituted with one or more halogen atoms;

Y and $Y_1$ are each independently hydrogen or $C_1$–$C_3$ alkyl;

===== represents a single bond;

W is $CH_2A$ or when taken together with $W_1$, $WW_1$ is, represented by the structure —$CH_2C(O)OC(O)$—;

$W_1$ is A or when taken together with W, $W_1W$ is represented by the structure —$C(O)OC(O)CH_2$—;

A is $C(O)OR_5$;

$R_5$ is hydrogen, $C_1$–$C_6$ alkyl or an alkali metal, alkaline earth metal, ammonium or organic ammonium cation; and the optical isomers thereof.

A most preferred group of safener compounds of the present invention are those wherein X is O;

Z, $Z_1$ and $Z_2$ are each independently hydrogen, $C_1$–$C_4$ alkoxy, F, Cl, Br, $C_1$–$C_4$ alkyl or phenoxy optionally substituted with one or more halogen atoms or $C_1$–$C_4$ alkyl groups optionally substituted with one or more halogen atoms, provided that at least one of Z—$Z_2$ is hydrogen and further provided that only one of Z—$Z_2$ is phenoxy optionally substituted with one or more halogen atoms or $C_1$–$C_4$ alkyl groups optionally substituted with one or more halogen atoms;

Y and $Y_1$ are each independently hydrogen or $C_1$–$C_3$ alkyl;

===== represents a single bond;

W is $CH_2A$ or when taken together with $W_1$, $WW_1$ is represented by the structure —$CH_2C(O)OC(O)$—;

$W_1$ is A or when taken together with W, $W_1W$ is represented by the structure —C(O)OC(O)CH$_2$—;

A is C(O)OR$_5$;

R$_5$ is hydrogen, C$_1$–C$_6$ alkyl or an alkali metal, alkaline earth metal, ammonium or organic ammonium cation; and the optical isomers thereof.

Another group of most preferred safener compounds of the present invention are those wherein X is S;

Z is hydrogen or Cl;

$Z_1$, $Z_2$, Y and $Y_1$ are hydrogen;

===== represents a single bond;

W is CH$_2$C(O)OR$_5$;

$W_1$ is C(O)OR$_5$; and

R$_5$ is hydrogen or an alkali metal, alkaline earth metal, ammonium or organic ammonium cation; and the optical isomers thereof, Among the formula I compounds of the present invention which are particularly useful for protecting crops from injury caused by a herbicide are the diammonium salt of 4-carboxy-3,4-dihydro-2H-1-benzopyran-4-acetic acid;

4-carboxy-3,4-dihydro-2H-1-benzopyran-4-acetic acid;

4-carboxy-6-[(2-chloro-α,α,α,6-tetrafluoro-p-tolyl)oxy-3,4-dihydro-2H-1-benzopyran-4-acetic acid;

4-carboxy-3,4-dihydro-6-methoxy-2H-1-benzopyran-4-acetic acid;

4-carboxy-6-chloro-3,4-dihydro-2H-1-benzopyran-4-acetic acid;

4-carboxy-8-chloro-3,4-dihydro-2H-1-benzopyran-4-acetic acid;

4-carboxy-6,8-dichloro-3,4-dihydro-2H-1-benzopyran-4-acetic acid;

4-carboxy-6,7-dichloro-3,4-dihydro-2H-1-benzopyran-4-acetic acid;

4-carboxy-6-fluoro-3,4-dihydro-2H-1-benzopyran-4-acetic acid;

7-bromo-4-carboxy-3,4-dihydro-2H-1-benzopyran-4-acetic acid;

6-bromo-4-carboxy-3,4-dihydro-2H-1-benzopyran-4-acetic acid;

8-bromo-4-carboxy-3,4-dihydro-2H-1-benzopyran-4-acetic acid;

4-carboxy-6,8-dibromo-3,4-dihydro-2H-1-benzopyran-4-acetic acid;

4-carboxy-6,8-dimethyl-3,4-dihydro-2H-1-benzopyran-4-acetic acid;

2,2',3,3',4',5'-hexahydrospiro[2H-1-benzopyran-4,3'-(2'H)-furan]-2',5'-dione;

4-carboxy-6-chloro-3,4-dihydro-2H-1-benzopyran-4-acetate, diethyl ester;

4-carboxy-6-fluoro-3,4-dihydro-2-methyl-2H-1-benzopyran-4-acetic acid as mixture of diastereomers;

4-carboxy-6-chloro-3,4-dihydro-2H-1-benzothiopyran-4-acetic acid;

4-carboxy-3,4-dihydro-2H-1-benzothiopyran-4-acetic acid; and 1-carboxy-1,2,3,4-tetrahydro-1-napthaleneacetic acid.

The present invention also provides compounds of formula II which are useful as safeners against herbicidal injury in important agronomic crops.

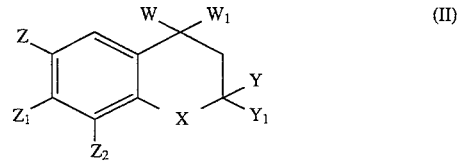

(II)

wherein

X is O or S(O)$_q$;

q is an integer of 0, 1 or 2;

Z, $Z_1$ and $Z_2$ are each independently hydrogen, F, Cl, Br, C$_1$–C$_4$ alkoxy, phenoxy optionally substituted with one or more halogen atoms or C$_1$–C$_4$ alkyl groups optionally substituted with one or more halogen atoms, or C$_1$–C$_4$ alkyl optionally substituted with one or more halogen atoms, C$_1$–C$_4$ alkoxy groups or hydroxy groups, provided that only one of Z—$Z_2$ is C$_1$–C$_3$ alkoxyalkyl or phenoxy optionally substituted with one or more halogen atoms or C$_1$–C$_4$ alkyl groups optionally substituted with one or more halogen atoms;

Y and $Y_1$ are each independently hydrogen, F, Cl or C$_1$–C$_3$ alkyl, provided that when $Y_2$ is F or Cl, then $Y_1$ is hydrogen;

W is CH$_2$A or when taken together with $W_1$, WW$_1$ is represented by the structure —CH$_2$C(O)OC(O)—;

$W_1$ is A or when taken together with W, $W_1W$ is represented by the structure —C(O)OC(O)CH$_2$—;

A is C(O)X$_1$ or CH(OR$_4$)$_2$;

X$_1$ is OR$_5$ or SR$_9$;

R$_5$ is hydrogen, C$_1$–C$_6$ alkyl, C$_3$–C$_6$ alkenyl, C$_3$–C$_6$ alkynyl or an alkali metal, alkaline earth metal, manganese, copper, zinc, cobalt, silver, nickel, ammonium or organic ammonium cation;

R$_9$ is hydrogen C$_1$–C$_6$ alkyl C$_3$–C$_6$ alkenyl or C$_3$–C$_6$ alkynyl;

R$_4$ is C$_1$–C$_6$ alkyl and when taken together R$_4$ and a second R$_4$ may form a ring in which R$_4$R$_4$ are represented by —(CH$_2$)$_2$— or —(CH$_2$)$_3$—; and the optical isomers thereof;

provided that when Y is hydrogen and $Y_1$ is hydrogen or C$_1$–C$_3$ alkyl, then one of Z, $Z_1$ or $Z_2$ is phenoxy optionally substituted with one or more halogen atoms or C$_1$–C$_4$ alkyl groups optionally substituted with one or more halogen atoms.

Preferred safener compounds of formula II are those wherein

X is O or S;

Z is phenoxy optionally substituted with one or more halogen atoms or C$_1$–C$_4$ alkyl groups optionally substituted with one or more halogen atoms;

$Z_1$ and $Z_2$ are each independently hydrogen, F, Cl, Br or C$_1$–C$_4$ alkyl optionally substituted with one or more halogen atoms, C$_1$–C$_4$ alkoxy groups or hydroxy groups;

Y and $Y_1$ are each independently hydrogen or C$_1$–C$_3$ alkyl;

W is CH$_2$C(O)OR$_5$;

$W_1$ is C(O)OR$_5$; and

R$_5$ is hydrogen, C$_1$–C$_6$ alkyl or an alkali metal, alkaline earth metal, ammonium or organic ammonium cation.

More preferred compounds of formula II which are particularly useful as safeners against herbicidal injury in important agronomic crops are those wherein X is O;

Z is phenoxy optionally substituted with one or more halogen atoms or $C_1$–$C_4$ alkyl groups optionally substituted with one or more halogen atoms;

$Z_1$ and $Z_2$ are each independently hydrogen, F, Cl or Br;

Y and $Y_1$ are each independently hydrogen;

W is $CH_2C(O)OR_5$;

$W_1$ is $C(O)OR_5$; and $R_5$ is hydrogen, $C_1$–$C_6$ alkyl or an alkali metal, alkaline earth metal, ammonium or organic ammonium cation.

Alkali metals include: sodium, potassium and lithium, but sodium is generally preferred. Further, the term "organic ammonium" is defined as a group consisting of a positively charged nitrogen atom joined to from one to four aliphatic groups, each containing from one to sixteen carbon atoms. Exemplary of halogen are fluorine, chlorine, bromine and iodine.

Certain formula I compounds may be prepared as shown below in flow diagram I.

Formula I compounds may also be prepared as shown below in flow diagram II.

FLOW DIAGRAM II

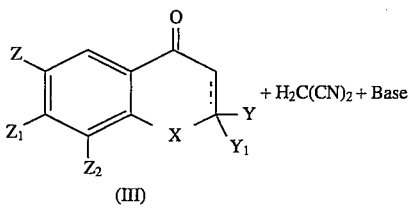

FLOW DIAGRAM I

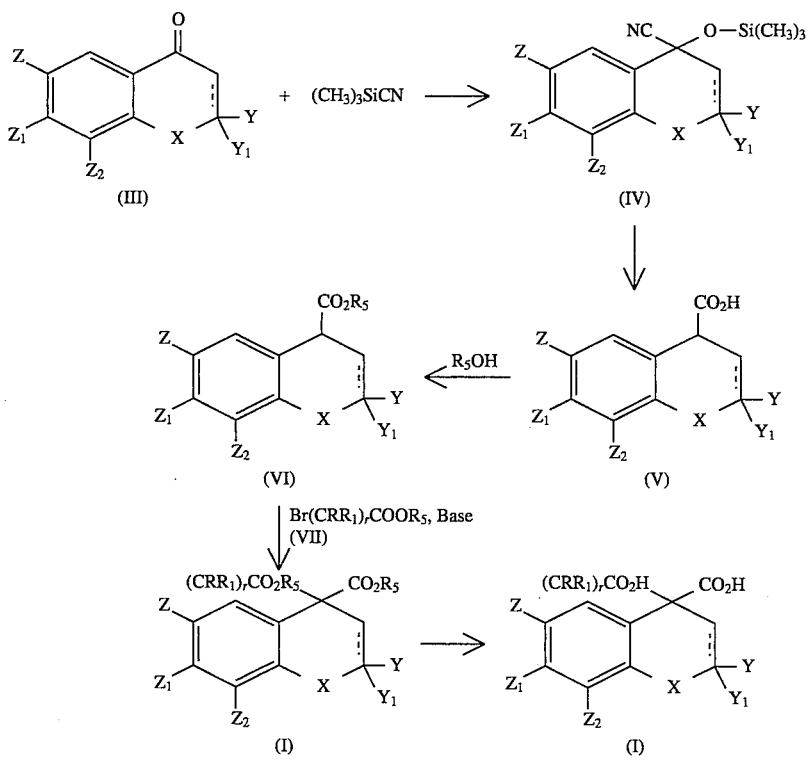

wherein $R_5$ is $C_3$–$C_{10}$ alkenyl, $C_3$–$C_{10}$ alkynyl, or $C_1$–$C_{10}$ alkyl optionally substituted with one or more halogen atoms.

The appropriately substituted formula III ketone is reacted with trimethylsilyl cyanide in the presence of a Lewis acid such as zinc iodide to form the formula IV compound. Hydrolysis of the formula IV compound gives the formula V acid which is esterified using standard procedures to obtain the formula VI ester. The formula VI ester is then alkylated with a formula VII bromo ester in the presence of a base such as sodium hydride and a solvent such as 1-methyl-2-pyrrolidinone to give the desired formula I diester. The formula I diester may be hydrolyzed under basic conditions to give the formula I diacid.

-continued
FLOW DIAGRAM II

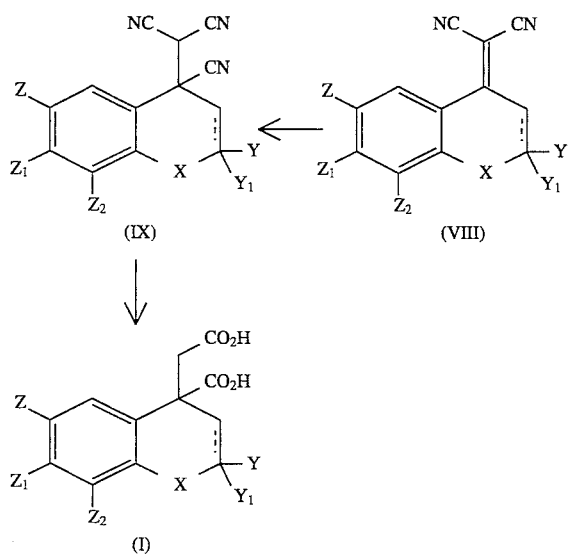

The appropriately substituted formula III ketone is reacted with malononitrile in the presence of a base such as pyridine to form the formula VIII compound. The formula VIII compound is reacted with potassium cyanide in the presence of water to form the formula IX compound which is hydrolyzed with acid or base to obtain the desired formula I diacid.

Other compounds of formula I may be prepared as shown below in flow diagram III.

FLOW DIAGRAM III

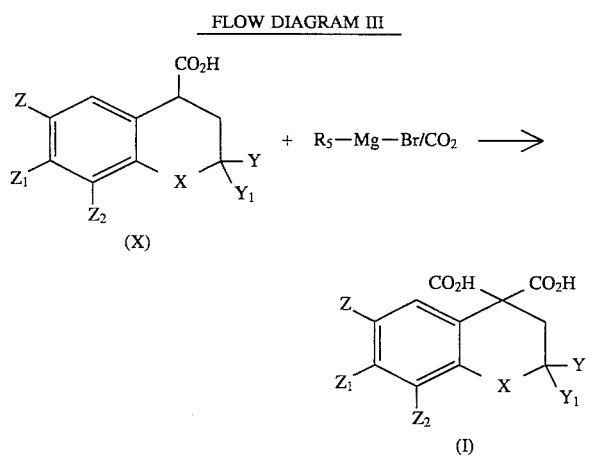

wherein $R_5$ is $C_1$–$C_{10}$ alkyl.

The appropriately substituted formula X carboxylic acid is reacted with a $C_1$–$C_{10}$ alkylmagnesium bromide compound and carbon dioxide to obtain the desired formula I compound.

Additional compounds of formula I may be prepared as shown below in flow diagram IV.

FLOW DIAGRAM IV

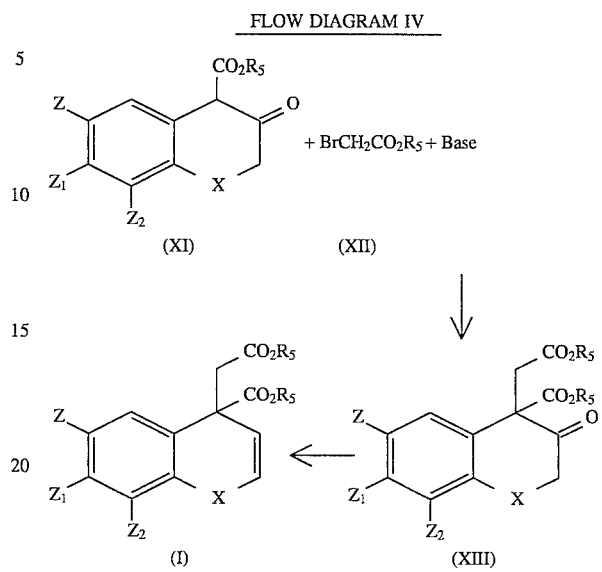

wherein $R_5$ is $C_1$–$C_{10}$ alkyl.

The appropriately substituted formula XI ketone is reacted with a formula XII bromo ester in the presence of a base to form a formula XIII compound which is reduced to form an intermediate alcohol which is converted to a suitable leaving group such as mesylate and eliminated to give the desired formula I compound.

Surprisingly, it has been found that the compounds of the present invention are especially useful for protecting crops from injury caused by a herbicidally effective amount of a herbicide by applying to the crop plant, the seed of the crop, or the soil or water surrounding the crop or crop seed an effective antidotal amount of a formula I compound.

Herbicides which are suitable for use in the present invention include imidazolinone herbicides such as
5-ethyl-2-(4-isopropyl-4-methyl-5-oxo-2-imidazolin-2-yl)nicotinic acid;
2-(4-isopropyl-4-methyl-5-oxo-2-imidazolin-2-yl)-3-quinolinecarboxylic acid;
isopropylammonium 2-(4-isopropyl-4-methyl-5-oxo-2-imidazolin-2-yl)nicotinate;
methyl 2-(4-isopropyl-4-methyl-5-oxo-2-imidazolin-2-yl)nicotinate;
mixture of methyl 2-(4-isopropyl-4-methyl-5-oxo-2-imidazolin-2-yl)-p-toluate and methyl 6-(4-isopropyl-4-methyl-5-oxo-2-imidazolin-2-yl)-m-toluate; and
2-(4-isopropyl-4-methyl-5-oxo-2-imidazolin-2-yl)-5-methylnicotinic acid;
sulfonylurea herbicides such as
methyl o-{{3-[4,6-bis(difluoromethoxy)-2-pyrimidinyl]ureido}sulfonyl}benzoate;
1-[(o-chlorophenyl)sulfonyl]-3-(4-methoxy-6-methyl-s-triazin-2-yl)urea;
methyl O-{{[3-(4,6-dimethoxy-2-pyrimidinyl)ureido]sulfonyl}methyl}benzoate;

methyl o-{[3-(4-methoxy-6-methyl-1,3,5-triazin-2-yl)ureido] sulfonyl}benzoate;
1-(4,6-dimethoxy-2-pyrimidinyl)-3-{[3-(dimethylcarbamoyl)- 2-pyridyl]sulfonylurea;
ethyl 5-{[3-(4,6-dimethoxy-2-pyrimidinyl)ureido]sulfonyl} -1-methylpyrazole-4-carboxylate;
methyl 3-{[3-(4-methoxy-6-methyl-1,3,5-triazin-2-yl)ureido] sulfonyl}-2-thiophenecarboxylate; and
1-{[o-(3-chloropropoxy)phenyl]sulfonyl}-3-(4-methoxy-6-methyl-1,3,5-triazin-2-yl)urea;
sulfamoylurea herbicides such as
1-{[o-(cyclopropylcarbonyl)phenyl]sulfamoyl}-3-(4,6 -dimethoxy-2-pyrimidinyl)urea;
1-[(o-acetylphenyl)sulfamoyl]-3-(4-methoxy-6-methyl-2-pyrimidinyl)urea; and
1-[(o-acetylphenyl)sulfamoyl]-3-(4,6-dimethoxy-2 -pyrimidinyl)urea;
oxime herbicides such as
2-(O-ethyloxime) of 2-butyryl-5-[2-(ethylthio)-propyl]-3-hydroxy-2-cyclohexen-1-one;
sodium salt of methyl 5-butyryl-2,2-dimethyl-4,6 -dioxocyclohexanecarboxylate, 5-(O-allyloxime);
2-[O-(3-chloroallyl)oxime of 5-[2-(ethylthio)propyl] -3-hydroxy-2-propionyl-2-cyclohexen-1-one;
2-(O-ethyloxime) of 2-butyryl-3-hydroxy-5-(tetrahydro-2H-thiopyran-3-yl)-2-cyclohexen-1-one; and
2-(O-ethyloxime) of 3-hydroxy-2-propionyl-5-(2,4,6 -trimethylphenyl)-2-cyclohexen-1-one;
2-(4-aryloxyphenoxy)propionic acid herbicides such as
methyl 2-{p-{[3-chloro-5-(trifluoromethyl)-2-pyridyl] oxy}phenoxy}propionate;
methyl 2-[p-(2,4-dichlorophenoxy)phenoxy]propionate;
butyl 2-{p-{[5-(trifluoromethyl)-2-pyridyl]oxy}phenoxy} propionate;
butyl 2-{p-{[5-(trifluoromethyl)-2-pyridyl]oxy}phenoxy} propionate, (R)-;
2-ethoxyethyl 2-{p-{[3-chloro-5-(trifluoromethyl)-2 -pyridyl]oxy}phenoxy}propionate;
1-{2-{p-[(3,5-dichloro-2-pyridyl)oxy]phenoxy}propionyl} isoxazolidine;
2-[(isopropylideneamino)oxy]ethyl 2-{p-[(6-chloro-2 -quinoxalinyl)oxy]phenoxy}propionate, (R)-;
ethyl 2-{p-[(6-chloro-2-quinoxalinyl)oxy] phenoxy}propionate;
ethyl 2-{p-[(6-chloro-2-benzoxazolyl)oxy] phenoxy}propionate;
N-benzoyl-N-(3,4-dichlorophenyl)alanine, ethyl ester;
2-[(2,4-dichloro-m-tolyl)oxy]-2-methylpropionanilide;
ethyl 2-{p-[(6-chloro-2-benzoxazolyl)oxy]phenoxypropionate;
ethyl 2-{p-[(6-chloro-2-benzothiazolyl)oxy]phenoxy} propionate;
N-benzoyl-N-(3-chloro-4-fluorophenyl)alanine, isopropyl ester;
N-benzoyl-N-(3-chloro-4-fluorophenyl)alanine, methyl ester; and
methyl p,α-dichlorohydrocinnamate;
thiocarbamate herbicides such as
ethyl dipropylthiolcarbamate;
S-ethyl diisobutylthiocarbamate;
S-propyl dipropylthiocarbamate;
S-ethyl hexahydro-1H-azepine-1-carbothioate;
S-(p-chlorobenzyl)diethylthiocarbamate; and
S-benzyl bis(1-methylpropyl)thiocarbamate;
2-chloroacetanilide herbicides such as
2-chloro-6'-ethyl-N-(2-methoxy-1-methylethyl)-o-acetotoluidide;
2-chloro-2',6'-diethyl-N-(methoxymethyl)acetanilide;
N-(butoxymethyl)-2-chloro-2'-ethylacetanilide;
2-chloro-2',6'-diethyl-N-(2-propoxyethyl)acetanilide; and
2-chloro-N-isopropylacetanilide;
dinitroaniline herbicides such as
N-(1-ethylpropyl)-3,4-dimethyl-2,6-dinitrobenzenamine;
α,α,α-trifluoro-2,6-dinitro-N,N-dipropyl-p-toluidine;
3,5-dinitro-$N^4,N^4$-dipropylsulfanilamide;
N-butyl-N-ethyl-α,α,α-trifluoro-2,6-dinitro-p-toluidine;
2,6-dinitro-N,N-dipropylcumidine; and
N-ethyl-α,α,α-trifluoro-N-(2-methylallyl)-2,6-dinitro-p-toluidine; and
isoxazolyl-2-imidazolidinone herbicides such as
3-(5-tert-butyl-3-isoxazolyl)-4-hydroxy-1-methyl-2-imidazolidinone; and
3-(5-tert-butyl-3-isoxazoyl)-1-methyl-2-oxo-4-imidazolidinyl methyl carbamate.

Although, many of these herbicides have been used with success in certain crops, they have been found to be phytotoxic in other crops, especially cereal crops. Surprisingly, it has been found that by applying a substituted benzopyran or tetrahydronaphthalene compound of formula I to the seed of the crop, the foliage of the crop or the soil or water surrounding the crop or crop seed the herbicide is safened.

The present invention also includes a safened herbicidal composition comprising a herbicide and a safener of the invention, a substituted benzopyran or tetrahydronaphthalene compound of formula I.

Safening of crops, especially cereal crops such as corn, sorghum, oat, wheat, barley and rice from the postemergence application of herbicides may be effected by allowing said crop plants to grow until the third to fourth leaf stage then spraying with an aqueous solution of the safener either alone or tank mixed with at least one of the above described herbicides. The tank mix should contain an effective amount of herbicide and an effective amount of safener. Although rates will naturally vary with the particular herbicide and crop, typical rates of application for the safener are about 0.063 kg/ha to 2.0 kg/ha.

The present invention may also be practiced by applying the herbicide and/or safener to the soil preemergence. A tank mix of the safener and herbicide may be conveniently prepared and employed or sequential sprayings may be used in accordance with the present method.

A wide variety of troublesome weed species can also be effectively controlled in the presence of important agronomic crops such as corn, sorghum, oat, wheat, barley and rice by safening the crop plants by any conventional seed treatment techniques or by uniformly coating the seeds with a 5% to 50% wettable powder composition of the safener, planting the coated seed in the usual manner, and spraying the soil with a herbicide or by incorporating the herbicide into the soil before the coated seeds have been planted or by allowing the crop plants from the coated seeds to grow until the third to fourth leaf stage then spraying with a herbicide. Although rates will vary with the particular herbicide and crop, typical rates of application are about 0.10 mg to 4.0 mg of safener per gram of crop seed.

In order to facilitate a further understanding of the invention, the following examples are presented primarily for the purpose of illustrating more specific details thereof. The examples utilize the above reaction schemes and also provide further means for preparing even more compounds of the present invention which are not specifically described above. The invention is not to be deemed limited thereby except as defined in the claims.

EXAMPLE 1

Preparation of
2,3-Dihydro-4H-1-benzothiopyran-Δ⁴,α-malononitrile

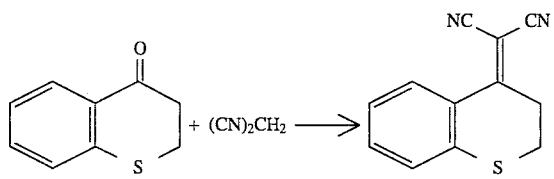

A mixture of 4-thiochromanone (50.0 g, 0.304 mol) and malononitrile (30.17 g, 0.457 mol) in pyridine is stirred at room temperature for several days, treated with additional malononitrile (30.17 g, 0.457 mol), stirred at room temperature for several days and diluted with a 0.5N hydrochloric acid/ether mixture. The diluted reaction mixture is filtered to obtain a solid which is dried overnight in a vacuum oven to give the title product as an orange solid (28.5 g, mp 116.5°–118.5° C.).

Using essentially the same procedure, but substituting the appropriate starting material for 4-thiochromanone, the following compounds are obtained:

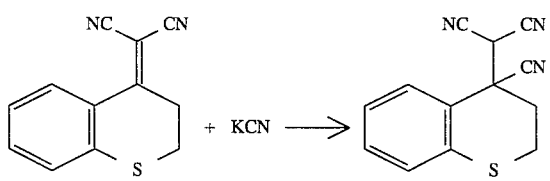

| X | Z | mp °C. |
|---|---|---|
| O | $C_6H_5$ | 147–149 |
| $CH_2$ | H | 100–105 |

EXAMPLE 2

Preparation of
4-Cyano-3,4-dihydro-2H-1-benzothiopyran-4-malononitrile

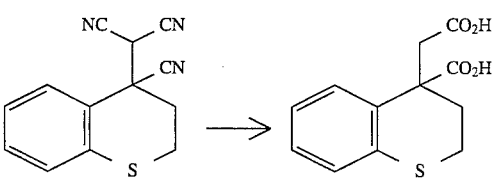

A mixture of 2,3-dihydro-4H-1-benzothiopyran-Δ⁴,α-malononitrile (20.0 g, 0.094 mol) in a 1:1 tetrahydrofuran/ethanol solution is treated dropwise with a solution of potassium cyanide (12.65 g, 0.188 mol) in water over 15 minutes. After stirring for 4 hours, the reaction mixture is added dropwise to a hydrochloric acid/ice mixture to obtain a solid which is extracted with ether. The combined organic extracts are dried over anhydrous $MgSO_4$ and concentrated in vacuo to give the title product as a pale yellow solid (21.73 g, mp 135.5°–137° C.).

Using essentially the same procedure, but substituting the appropriate starting material for 2,3-dihydro-4H-1-benzothiopyran-Δ⁴,α-malononitrile, the following compounds are obtained:

| X | Z | mp °C. |
|---|---|---|
| O | $C_6H_5$ | 171–173 |
| $CH_2$ | H | |

EXAMPLE 3

Preparation of
4-Carboxy-3,4-dihydro-2H-1-benzothiopyran-4-acetic acid

A mixture of 4-cyano-3,4-dihydro-2H-1-benzothiopyran-4-malononitrile (20.5 g, 0,086 mol) in 1:1 acetic acid/hydrochloric acid is heated at reflux for 5 days, cooled to room temperature and filtered to obtain a solid. The solid is washed with water and dried in a vacuum oven to give the title product as a red solid (13.54 g, mp 168°–170° C.).

Using essentially the same procedure, but substituting the appropriate starting material for 4-cyano-3,4-dihydro-2H-1-benzothiopyran-4-malononitrile, the following compounds are obtained:

| X | Z | mp °C. |
|---|---|---|
| O | $C_6H_5$ | 200–202.5 |
| $CH_2$ | H | 146–148 |

EXAMPLE 4

Preparation of 3-(2,4-Dichlorophenoxy)-1-propanol

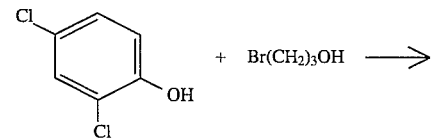

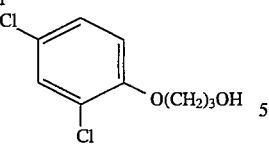

A solution of 3-bromopropanol (53.86 g, 0.368 mol) in isopropanol is added dropwise to a mixture of 2,4-dichlorophenol (50 g, 0.307 mol) and 1,8-diazabicyclo[ 5.4.0] undec-7-ene (70.05 g, 0.406 mol) in isopropanol at reflux. The reaction mixture is heated at reflux for 3 hours and concentrated in vacuo to obtain a residue. The residue is dissolved in methylene chloride and the organic solution is washed sequentially with 0.5N sodium hydroxide solution, 1M hydrochloric acid and brine, dried over MgSO$_4$ and concentrated in vacuo to obtain an oil which solidifies to give the title product as a white solid (71.9 g, mp 53°–55° C.).

Using essentially the same procedure, but substituting 4-phenylphenol for 2,4-dichlorophenol, 3-(4-phenylphenoxy)-1-propanol is obtained, mp 123°–124° C.

EXAMPLE 5

Preparation of 3-(2,4-Dichlorophenoxy)propionic acid

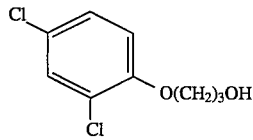  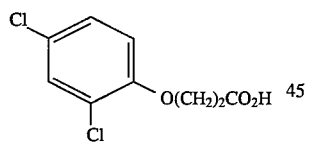

Jones reagent (2.3M, 0.283L, 0.650 mol, CrO$_3$/H$_2$SO$_4$) is added to a solution of 3-(2,4-dichlorophenoxy)-1-propanol (71.87 g, 0.325 mol) in acetone while maintaining the temperature of the reaction mixture below 40° C. After the addition is complete, isopropanol is added and the reaction mixture is filtered through diatomaceous earth. The filtrate is concentrated in vacuo to give a blue-green solid which is partitioned between ether and water. The organic phase is separated, washed with brine, dried over anhydrous MgSO$_4$ and concentrated in vacuo to obtain the title product as a yellow solid (69.87 g, mp 93°–95° C.).

Using essentially the same procedure, but substituting 3-(4-phenylphenoxy)-1-propanol for 3-(2,4-dichlorophenoxy)-1-propanol, 3-(4-phenylphenoxy)propionic acid is obtained, mp 173°–176° C.

EXAMPLE 6

Preparation of 6,8-Dichloro-2,3-dihydro-4H-1-benzopyran-4-one

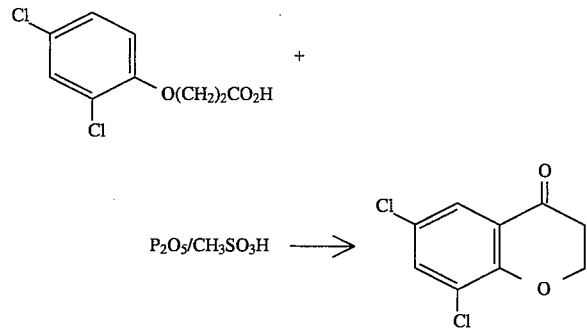

3-(2,4-Dichlorophenoxy)propionic acid (52.36 g, 0.223 mol) is added portion-wise to a mixture of phosphorus pentoxide (70.98 g, 0.490 mol) in methanesulfonic acid (Eaton's reagent) under nitrogen. The reaction mixture is stirred at room temperature for 4 hours, poured into water and filtered to obtain a solid. The solid is washed with water and dried in a vacuum oven to give the title product as an off-white solid (45.88 g, mp 86°–87° C.).

Using essentially the same procedure, but substituting the 3-(4-phenylphenoxy)propionic acid for 3-(2,4-dichlorophenoxy)propionic acid, 6-phenyl- 2,3-dihydro-4H-1-benzopyran-4-one is obtained, mp 74°–75° C.

EXAMPLE 7

Preparation of 4,6-Dicarboxy-3,4-dihydro-2H-1-benzopyran-4-acetic acid

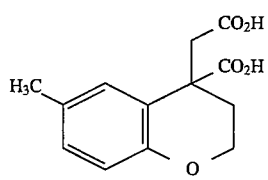 + NaOH +

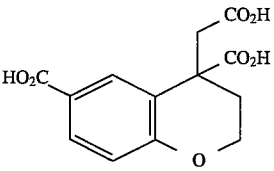

Potassium permanganate (7.52 g, 48 mmol) is added to a mixture of 4-carboxy-3,4-dihydro-6-methyl-2H-benzopyran-4-acetic acid (3.50 g, 14 mmol) and sodium hydroxide (0.84 g, 21 mmol) in water at 50° C. The reaction mixture is stirred at 50° to 60° C. overnight and filtered through diatomaceous earth. The filtrate is acidified to pH 1 with hydrochloric acid, washed with an ether/methylene chloride solution and filtered to obtain the title product as a white solid (0.62 g, mp 198°–200° C.).

EXAMPLE 8

Preparation of
6-Amino-4-carboxy-3,4-dihydro-2H-1
-benzopyran-4-acetic acid

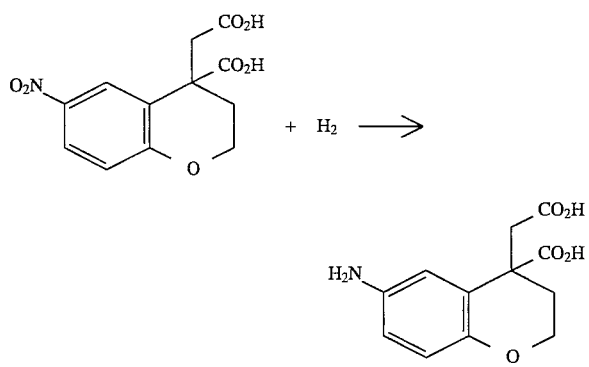

A mixture of 4-carboxy-3,4-dihydro-6-nitro-2H-1-benzopyran-4-acetic acid (4.1 g, 14 mmol), 10% palladium on carbon (1.6 g) and sulfuric acid (1 mL) in ethanol is hydrogenated at 45 psi for 2 hours and filtered through diatomaceous earth. The filtrate is concentrated in vacuo to obtain the title product as a tan solid (2.6 g) which is identified by $^1$H and $^{13}$CNMR spectral analyses.

EXAMPLE 9

Preparation of
4-Carboxy-3,4-dihydro-6-hydroxy-2H-1
-benzopyran-4-acetic acid and
4-carboxy-3,4-dihydro-
6-methoxy-2H-1-benzopyran-4-acetic acid

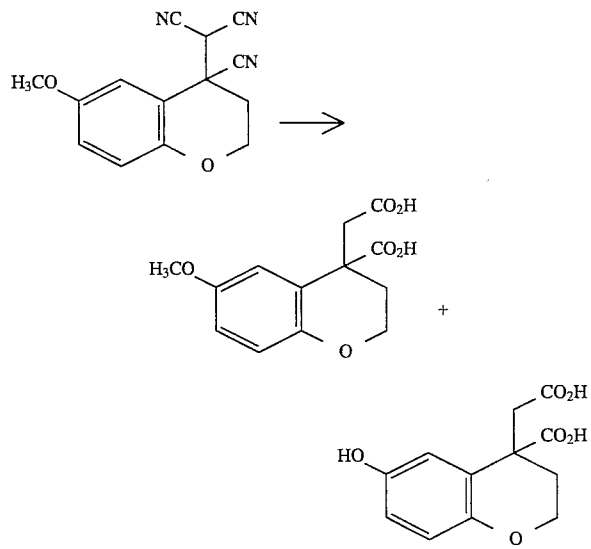

Concentrated hydrochloric acid is added to a mixture of 4-cyano-3,4-dihydro-6-methoxy-2H-1-benzopyran- 4-malononitrile (42.76 g, 0.1688 mol) in acetic acid at 30° C. The reaction mixture is heated at reflux for three days, cooled and concentrated in vacuo to give a brown solid. The solid is stirred in an ether/water mixture, filtered, washed sequentially with ether and water and dried to obtain 4-carboxy-3,4-dihydro-6-hydroxy-2H-1-benzopyran-4-acetic acid as a gray solid (10.25 g) which is identified by $^1$H and $^{13}$CNMR spectral analyses.

The filtrate is concentrated in vacuo and partitioned between ether and water. The organic phase is separated and the aqueous phase is extracted with ether. The organic extracts are combined with the organic phase and the organic solution is extracted with 5% sodium hydroxide solution. The 5% sodium hydroxide extracts are acidified with hydrochloric acid, filtered and dried to obtain a solid. The solid is chromatographed using silica gel and a 4:6 acetone/methylene chloride solution to obtain 4-carboxy-3,4-dihydro-6-methoxy-2H-1-benzopyran-4-acetic acid as a brown solid (1.72 g) which is identified by $^1$H and $^{13}$CNMR spectral analyses.

EXAMPLE 10

Preparation of
4-Carboxy-6-(hexyloxy)-3,4-dihydro-2H-
1-benzopyran-4-acetic acid, dihexyl ester

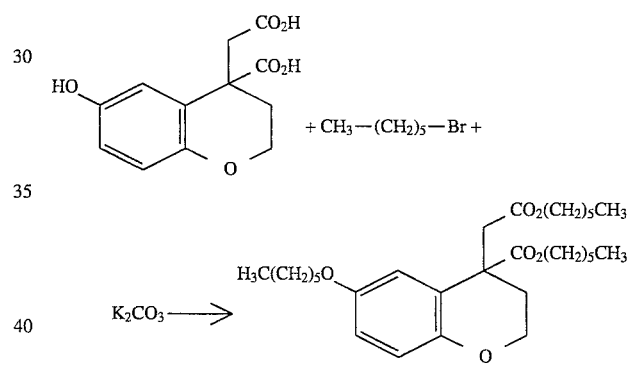

A mixture of 4-carboxy-3,4-dihydro-6 -hydroxy-2H-1-benzopyran-4-acetic acid (0.75 g, 2.97 mmol) and potassium carbonate (1.44 g, 10.40 mmol) in N,N-dimethylformamide is heated to 105° C., cooled to room temperature, treated with n-hexylbromide (0.98 g, 5.94 mmol), heated at 60° C. to 90° C. overnight, treated with additional n-hexylbromide (0.98 g, 5.94 mmol), heated at 125° C. overnight, cooled to room temperature and diluted with water. The aqueous mixture is extracted with ether. The combined organic extracts are washed sequentially with 10% sodium hydroxide solution, water and brine, dried over anhydrous MgSO$_4$ and concentrated in vacuo to obtain a brown syrup. Flash chromatography of the syrup using silica gel and a 1:1 hexanes/methylene chloride solution gives the title product as a pale yellow oil, 1.04 g, which is identified by $^1$H and $^{13}$CNMR spectral analyses.

Using essentially the same procedure, but substituting allylbromide for n-hexylbromide, 6-(allyloxy)- 4-carboxy-3,4-dihydro-2H-1-benzopyran-4-acetic acid, diallyl ester is obtained as a pale yellow liquid.

EXAMPLE 11

Preparation of
3,4-dihydro-6-hydroxy,2H-1-benzopyran-4-acetic
acid, 4-carboxylic acid, allyl ester

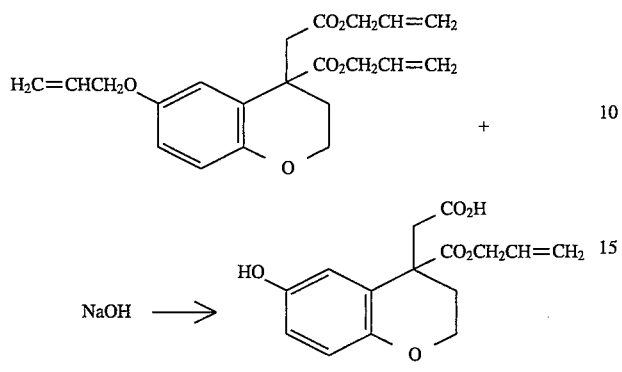

A mixture of 6-(allyloxy)-4-carboxy-3,4-dihydro-2H-1-benzopyran-4-acetic acid, diallyl ester (0.95 g, 2.55 mmol) and sodium hydroxide (0.26 g, 6.38 mmol) in a water/methanol mixture is heated at reflux overnight, concentrated in vacuo and diluted with water. The aqueous mixture is acidified to about pH 1 with 10% hydrochloric acid and extracted with ether. The combined organic extracts are washed sequentially with water and brine, dried over MgSO$_4$ and concentrated in vacuo to obtain a beige solid. The solid is chromatographed using silica gel and a 2:3 ether/methylene chloride solution to give the title product as a beige solid (0.75 g, mp 147.5°–150° C.) which is identified by $^1$H and $^{13}$CNMR spectral analyses.

Using essentially the same procedure, but substituting 4-carboxy-6-(hexyloxy)-3,4-dihydro-2H-1-benzopyran-4-acetic acid, dihexyl ester for 6-(allyloxy)-4-carboxy-3,4-dihydro-2H-1-benzopyran-4-acetic acid, diallyl ester; 3,4-dihydro-6-hydroxy-2H-1-benzopyran-4-acetic acid, 4-carboxylic acid, hexyl ester is obtained as a solid.

EXAMPLE 12

Preparation of
4-Carboxy-6-[(2-chloro-α,α,α,6-tetrafluoro-p-tolyl)oxy]-3,4-dihydro-2H-1-benzopyran-4-acetic acid

TABLE XII

| Treatment | Rate (kg/ha) | (mg/g of seed) | % Growth Reduction |
|---|---|---|---|
| G | 0.01 | | 17 |
| G + A | 0.01 | 0.25 | 15 |
| G + A | 0.01 | 0.50 | 7 |
| G + A | 0.01 | 1.0 | −2 |
| G + A | 0.01 | 2.0 | −1 |
| G + A | 0.01 | 4.0 | −14 |
| G | 0.025 | | 30 |
| G + A | 0.025 | 0.25 | 41 |
| G + A | 0.025 | 0.50 | 38 |
| G + A | 0.025 | 1.0 | 45 |
| G + A | 0.025 | 2.0 | 16 |
| G + A | 0.025 | 4.0 | 15 |

A mixture of 4-carboxy-3,4-dihydro-6-hydroxy-2H-1-benzopyran-4-acetic acid (0.50 g, 1.98 mmol) and potassium carbonate (0.96 g, 6.94 mmol) in N,N-dimethylformamide is heated to 105° C., cooled to 60° C., treated with 3-chloro-α,α,α,4,5-pentafluorotoluene (0.51 g, 2.38 mmol), stirred at room temperature overnight, treated with additional potassium carbonate (0.48 g) and 3-chloro-α,α,α,4,5-pentafluorotoluene (0.51 g), heated at 100° C. for three hours, cooled to room temperature and diluted with water. The aqueous mixture is basified with 10% sodium hydroxide solution and washed with ether. The washed aqueous mixture is acidified to about pH 1 with 10% hydrochloric acid and extracted with ether. The combined organic extracts are washed sequentially with water and brine, dried over MgSO$_4$ and concentrated in vacuo to obtain a tan foam. The foam is stirred in carbon tetrachloride at reflux and filtered to obtain the title product as a yellow solid (0.6 g, mp 205°–208° C.).

EXAMPLE 13

Preparation of
6-Chloro-3,4-dihydro-4-(trimethylsiloxy)-2H-1-benzothiopyran-4-carbonitrile

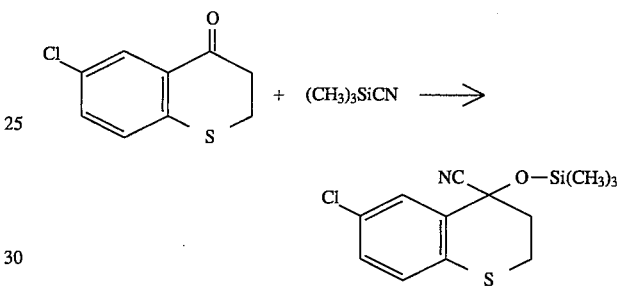

Under a nitrogen atmosphere, trimethylsilyl cyanide (50.0 g, 0.51 mol) is added to a mixture of 6-chloro-2,3-dihydro-4H-1-benzothiopyran-4-one (25.0 g, 0.126 mol) and anhydrous zinc iodide (1.1 g, 0.0034 mol) over 20 minutes. The reaction mixture is stirred at room temperature for 2 days, diluted with chloroform, washed with sodium hydrogen carbonate solution, dried and concentrated in vacuo to give the title product as a red oil (38.46 g) which is identified by $^1$H and $^{13}$CNMR spectral analyses.

Using essentially the same procedure but substituting 6,8-dichloro-2,3-dihydro-4H-1-benzopyran-4-one for 6-chloro-2,3-dihydro-4H-1-benzothiopyran-4-one, 6,8-dichloro-3,4-dihydro-4-(trimethylsiloxy)-2H-1-benzopyran-4-carbonitrile is obtained as a yellow solid, mp 77°–79° C.

EXAMPLE 14

Preparation of
6-Chloro-3,4-dihydro-2H-1-benzothiopyran-4-carboxylic acid

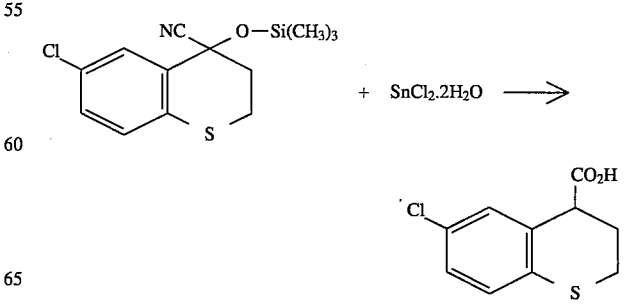

A mixture of tin(II) chloride dihydrate (115.42 g, 0.51 mol) and 6-chloro-3,4-dihydro-4-(trimethylsiloxy)- 2H-1-benzothiopyran-4-carbonitrile (37.53 g, 0.126 mol) in 1:1 acetic acid/concentrated hydrochloric acid is heated at reflux under nitrogen for 3 days, cooled to room temperature and diluted with chloroform. The aqueous phase is separated and extracted with chloroform. The organic phase and organic extracts are combined and extracted with 2N sodium hydroxide solution. The combined aqueous extracts are washed with chloroform and acidified to pH 3. The acidic aqueous mixture is extracted with chloroform and the combined organic extracts are dried and concentrated in vacuo to obtain a residue. The residue is triturated with an ether/petroleum ether mixture and filtered to give the title product as an off-white solid (12.56 g, mp 139°–150° C.).

Using essentially the same procedure but substituting 6,8-dichloro-3,4-dihydro-4-(trimethylsiloxy)- 2H-1-benzopyran-4-carbonitrile for 6-chloro- 3,4-dihydro-4-(trimethylsiloxy)-2H-1-benzothiopyran- 4-carbonitrile, 6,8-dichloro-3,4-dihydro-2H-1-benzopyran- 4-carboxylic acid is obtained as a brown oil.

EXAMPLE 15

Preparation of Ethyl
6-chloro-3,4-dihydro-2H-1-benzothiopyran-
4-carboxylate

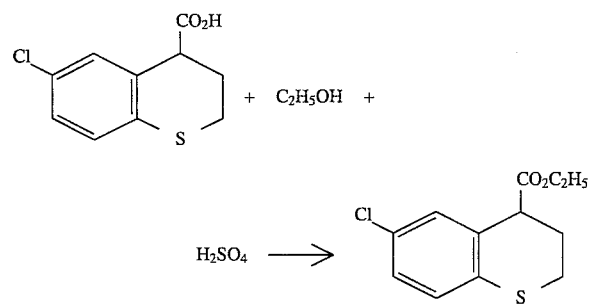

A mixture of 6-chloro-3,4-dihydro-2H-1-benzothiopyran- 4-carboxylic acid (12.56 g, 0.055 mol) and concentrated sulfuric acid (20 mL) in ethanol is heated at reflux for 29 hours, cooled, concentrated in vacuo and diluted with a water/methylene chloride mixture. The aqueous phase is separated and extracted with methylene chloride. The organic phase and organic extracts are combined, dried, decolorized with activated carbon and concentrated in vacuo to give the title product as a pale yellow oil (12.34 g) which is identified by $^1$H and $^{13}$CNMR spectral analyses.

Using essentially the same procedure, but substituting 6,8-dichloro-3,4-dihydro-2H-1-benzopyran- 4-carboxylic acid for 6-chloro-3,4-dihydro-2H-1-benzothiopyran-4-carboxylic acid, ethyl 6,8-dichloro- 3,4-dihydro-2H-1-benzopyran-4-carboxylate is obtained as a yellow oil.

EXAMPLE 16

Preparation of Diethyl
4-carboxy-6-chloro-3,4-dihydro-
2H-1-benzothiopyran-4-acetate

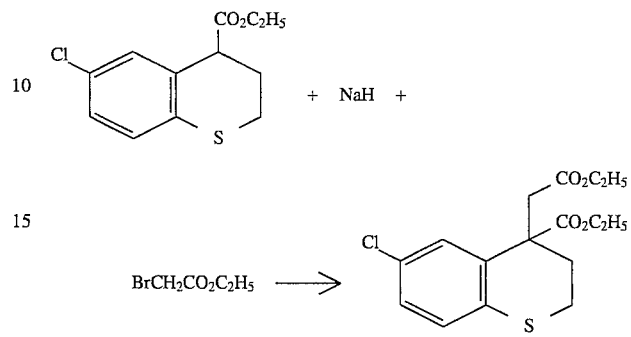

A suspension of sodium hydride (1.43 g, 80% real, 0.048 mol) in 1-methyl-2-pyrrolidinone is treated dropwise with a solution of ethyl 6-chloro-3,4-dihydro-2H-1-benzothiopyran-4-carboxylate (10.64 g, 0.041 mol) in 1-methyl-2-pyrrolidinone over 15 minutes under a nitrogen atmosphere. After stirring for one hour, the reaction mixture is cooled in an ice bath, treated dropwise with ethyl bromoacetate (8.18 g, 0.048 mol), stirred for 5 hours at room temperature, quenched with acetic acid and diluted with a water/methylene chloride mixture. The aqueous phase is separated and extracted with methylene chloride. The organic phase and methylene chloride extracts are combined, washed with water, dried, decolorized with activated carbon and concentrated in vacuo to obtain a residue. The residue is chromatographed using silica gel and a 100:0 to 19:1 hexanes/ethyl acetate solution to give the title product as a yellow oil (10.47 g) which is identified by $^1$H and $^{13}$CNMR spectral analyses.

Using essentially the same procedure, but substituting ethyl 6,8-dichloro-3,4-dihydro-2H-1 -benzopyran-4-carboxylate for ethyl 6-chloro-3,4-dihydro- 2H-1-benzothiopyran-4-carboxylate, diethyl 4-carboxy-6,8-dichloro-3,4-dihydro-2H-1-benzopyran-4 -acetate is obtained as a yellow oil.

EXAMPLE 17

Preparation of
4-Carboxy-6-chloro-3,4-dihydro-2H-1
-benzothiopyran-4-acetic acid

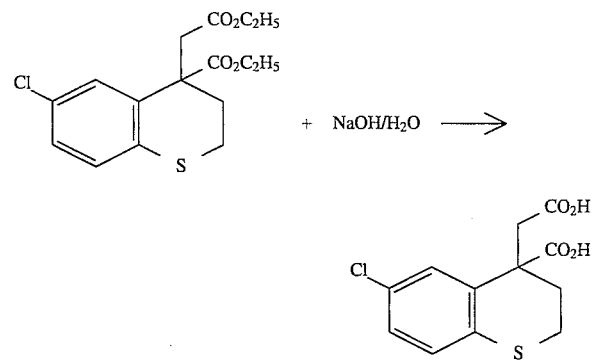

A solution of diethyl 4-carboxy-6-chloro-3,4-dihydro-2H-1-benzothiopyran-4-acetate (8.48 g, 0.025 mol) and 1N sodium hydroxide solution (74.2 mL, 0.074 mol) in 1:1 tetrahydrofuran/water is heated at reflux for 48 hours, cooled, concentrated in vacuo, washed with ether, acidified to pH 2.3, stirred in an ice bath for 20 minutes and filtered to obtain a solid. The solid is dried overnight in a vacuum oven to obtain the title product as a white solid (6.81 g, mp 189°–200° C. dec.).

EXAMPLE 18

Evaluation of the diammonium salt of 4-Carboxy-3,4-dihydro-2H-1-benzopyran-4-acetic acid as a safener for corn injury from postemergence applications of herbicides Corn plants (Pioneer 3475) in the third leaf stage are sprayed with a formulation of the appropriate herbicide, or a formulation of the appropriate herbicide mixed with a formulation of the diamonium salt of 4-carboxy-3,4-dihydro-2H-1-benzopyran-4-acetic acid. The herbicide and safener are diluted with water to provide the equivalent of 0.0015 kg/ha to 0.25 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2–4 weeks after treatment, the tests are terminated and each pot is examined and rated by measuring the height of the foliage. The test results are averaged and expressed as a percent growth reduction compared to an untreated check, using the following formula:

$$\% \text{ Growth Reduction} = 100 - \left[ \frac{\text{Height of Treated Plants}}{\text{Height of Untreated Plants}} \times 100 \right]$$

The results are summarized in Table I wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-6-methyl-S-triazin-2-yl)urea;

D is 1-[(o-acetylphenyl)sulfamoyl]-3-(4-methoxy-6-methyl-2-pyrimidinyl)urea;

E is 2-(4-isopropyl-4-methyl-5-oxo-2-imidazolin-2-yl)-5-methylnicotinic acid;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

I is 3-{p-[(3,5-dichloro-2-pyridyl)oxy]phenoxy}-2-hydroxybutyronitrile ethyl carbonate;

J is methyl (RS)-2-[4-(3-chloro-5-trifluoromethyl-2-pyridyloxy)phenoxy]propionate;

K is 3-(5-tert-butyl-3-isoxazolyl)-4-hydroxy-1-methyl-2-imidazolidinone;

L is 2-(O-ethyloxime) of 2-butyryl-5-[2-(ethylthio)propyl]-3-hydroxy-2-cyclohexen-1-one;

M is ethyl 2-{p-[(6-chloro-2-benzoxazolyl)oxy]phenoxy}propionate;

N is ethyl o-{[(4-chloro-6-methoxy-2-pyrimidinyl)carbamoyl]sulfamoyl}benzoate;

O is 1-[(o-acetylphenyl)sulfamoyl]-3-(4,6-dimethoxy-2-pyrimidinyl)urea; and

P is 1-{[o-(cyclopropylcarbonyl)phenyl]sulfamoyl}-3-(4,6-dimethoxy-2-pyrimidinyl)urea.

TABLE I

| Treatment | Rate (kg/ha) | % Growth Reduction |
|---|---|---|
| B | 0.075 | 23 |
| B + A | 0.075 + 0.50 | 2 |
| B | 0.10 | 29 |
| B + A | 0.10 + 0.50 | 10 |
| C | 0.0015 | 67 |
| C + A | 0.0015 + 0.50 | 18 |
| C | 0.003 | 68 |
| C + A | 0.003 + 0.50 | 15 |
| D | 0.003 | 68 |
| D + A | 0.003 + 0.50 | 60 |
| E | 0.05 | 28 |
| E + A | 0.05 + 0.50 | 6 |
| E | 0.075 | 71 |
| E + A | 0.075 + 0.50 | 4 |
| F | 0.05 | 10 |
| F + A | 0.05 + 0.50 | 10 |
| F | 0.10 | 59 |
| F + A | 0.10 + 0.50 | 18 |
| G | 0.012 | 67 |
| G + A | 0.012 + 0.50 | 29 |
| G | 0.025 | 65 |
| G + A | 0.025 + 0.50 | 63 |
| H | 0.012 | 61 |
| H + A | 0.012 + 0.50 | 41 |
| H | 0.025 | 66 |
| H + A | 0.025 + 0.50 | 63 |
| I | 0.10 | 41 |
| I + A | 0.10 + 0.50 | 0 |
| I | 0.25 | 63 |
| I + A | 0.25 + 0.50 | 19 |
| I | 0.012 | 67 |
| J + A | 0.012 + 0.50 | 63 |
| J | 0.025 | 66 |
| J + A | 0.025 + 0.50 | 65 |
| K | 0.05 | 19 |
| K + A | 0.05 + 0.50 | 27 |
| K | 0.10 | 58 |
| K + A | 0.10 + 0.50 | 41 |
| L | 0.025 | 38 |
| L + A | 0.025 + 0.50 | 3 |
| L | 0.05 | 68 |
| L + A | 0.05 + 0.50 | 39 |
| M | 0.012 | 75 |
| M + A | 0.012 + 0.50 | 75 |
| N | 0.025 | 46 |
| N + A | 0.025 + 0.50 | 22 |
| N | 0.05 | 53 |
| N + A | 0.05 + 0.50 | 28 |
| O | 0.012 | 6 |
| O + A | 0.012 + 0.50 | 5 |
| O | 0.025 | 39 |
| O + A | 0.025 + 0.50 | 9 |
| P | 0.012 | 0 |
| P + A | 0.012 + 0.50 | −7 |
| P | 0.025 | 15 |
| P + A | 0.025 + 0.50 | −3 |

EXAMPLE 19

Evaluation of the diammonium salt of 4-Carboxy-3,4-dihydro-2H-1-benzopyran-4-acetic acid as a safener for winter barley injury from postemergence applications of herbicides Winter barley plants (Volga) approximately 4 to 5 inches tall are sprayed with a formulation of the appropriate herbicide, or a formulation of the appropriate herbicide mixed with a formulation of the diammonium salt of 4-carboxy-3, 4-dihydro-2H-1-benzopyran- 4-acetic acid. The herbicide and safener are diluted with water to provide the equivalent of 0.012 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table II wherein

A is the diammonium salt of 4-carboxy-3,4-dihydro-2H-1 -benzopyran-4-acetic acid;

B is methyl o-{{3-[4,6-bis(difluoromethoxy)-2-pyrimidinyl] ureido}sulfonyl}benzoate;

C is 1-[(o-chlorophenyl)sulfonyl]-3-(4-methoxy-6-methyl- S-triazin-2-yl)urea;

D is 1-[(o-acetylphenyl)sulfamoyl]-3-(4-methoxy-6 -methyl-2-pyrimidinyl)urea;

E is 2-(4-isopropyl-4-methyl-5-oxo-2-imidazolin-2 -yl)-5-methylnicotinic acid;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2 -imidazolin-2-yl)nicotinate;

I is 3-{p-[(3,5-dichloro-2-pyridyl)oxy]phenoxy}-2 -hydroxybutyronitrile ethyl carbonate;

J is methyl (RS)-2-[4-(3-chloro-5-trifluoromethyl- 2-pyridyloxy)phenoxy]propionate;

L is 2-(O-ethyloxime) of 2-butyryl-5-[2-(ethylthio)propyl] -3-hydroxy-2-cyclohexen-1-one;

M is ethyl 2-{p-[(6-chloro-2-benzoxazolyl)oxy]phenoxy} propionate;

N is ethyl o-{[(4-chloro-6-methoxy-2-pyrimidinyl)carbamoyl] sulfamoyl}benzoate;

O is 1-[(o-acetylphenyl)sulfamoyl]-3-(4,6-dimethoxy-2 -pyrimidinyl)urea;

P is 1-{[o-(cyclopropylcarbonyl)phenyl]sulfamoyl}-3-( 4,6-dimethoxy-2-pyrimidinyl)urea; and Q is methyl 2-(4-isopropyl-4-methyl-5-oxo-2-imidazolin-2-yl)nicotinate.

TABLE II

| Treatment | Rate (kg/ha) | % Growth Reduction |
|---|---|---|
| B | 0.075 | 69 |
| B + A | 0.075 + 0.50 | 69 |
| B | 0.10 | 71 |
| B + A | 0.10 + 0.50 | 69 |
| C | 0.05 | 16 |
| C + A | 0.05 + 0.50 | 22 |
| C | 0.10 | 30 |
| C + A | 0.10 + 0.50 | 27 |
| D | 0.025 | 55 |
| D + A | 0.025 + 0.50 | 48 |
| D | 0.05 | 56 |
| D + A | 0.05 + 0.50 | 59 |
| E | 0.05 | 65 |

TABLE II-continued

| Treatment | Rate (kg/ha) | % Growth Reduction |
|---|---|---|
| E + A | 0.05 + 0.50 | 59 |
| E | 0.075 | 68 |
| E + A | 0.075 + 0.50 | 67 |
| F | 0.05 | 22 |
| F + A | 0.05 + 0.50 | 17 |
| F | 0.10 | 32 |
| F + A | 0.10 + 0.50 | 35 |
| G | 0.012 | 67 |
| G + A | 0.012 + 0.50 | 62 |
| G | 0.025 | 69 |
| G + A | 0.025 + 0.50 | 66 |
| H | 0.012 | 54 |
| H + A | 0.012 + 0.50 | 50 |
| H | 0.025 | 68 |
| H + A | 0.025 + 0.50 | 67 |
| I | 0.25 | −14 |
| I + A | 0.25 + 0.50 | −17 |
| I | 0.50 | −14 |
| I + A | 0.50 + 0.50 | −19 |
| J | 0.012 | 46 |
| J + A | 0.012 + 0.50 | 19 |
| J | 0.025 | 56 |
| J + A | 0.025 + 0.50 | 55 |
| L | 0.10 | 13 |
| L + A | 0.10 + 0.50 | 11 |
| L | 0.25 | 30 |
| L + A | 0.25 + 0.50 | 31 |
| M | 0.025 | 26 |
| M + A | 0.025 + 0.50 | 2 |
| M | 0.05 | 24 |
| M + A | 0.05 + 0.50 | 16 |
| N | 0.025 | 56 |
| N + A | 0.025 + 0.50 | 58 |
| N | 0.05 | 67 |
| N + A | 0.05 + 0.50 | 62 |
| O | 0.25 | 12 |
| O + A | 0.25 + 0.50 | 11 |
| O | 0.50 | 29 |
| O + A | 0.50 + 0.50 | 15 |
| P | 0.012 | −7 |
| P + A | 0.012 + 0.50 | −8 |
| P | 0.025 | 1 |
| P + A | 0.025 + 0.50 | −11 |
| Q | 0.025 | 31 |
| Q + A | 0.025 + 0.50 | 18 |
| Q | 0.05 | 29 |
| Q + A | 0.05 + 0.50 | 18 |

EXAMPLE 20

Evaluation of the diammonium salt of 4-Carboxy-3,4 -dihydro-2H-1-benzopyran-4-acetic acid as a safener for sorghum injury from postemergence applications of herbicides Sorghum plants (NC 271) approximately 4 to 5 inches tall are sprayed with a formulation of the appropriate herbicide, or a formulation of the appropriate herbicide mixed with a formulation of the diammonium salt of 4-carboxy-3,4-dihydro-2H-1-benzopyran- 4-acetic acid. The herbicide and safener are diluted with water to provide the equivalent of 0.0015 kg/ha to 0.25 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table III wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-6 -methyl-S-triazin-2-yl)urea;

D is 1-[(o-acetylphenyl)sulfamoyl]-3-(4-methoxy-6 -methyl-2-pyrimidinyl)urea;

E is 2-(4-isopropyl-4-methyl-5-oxo-2-imidazolin-2-yl)-5-methylnicotinic acid;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

I is 3-{p-[(3,5-dichloro-2-pyridyl)oxy]phenoxy}-2 -hydroxybutyronitrile ethyl carbonate;

J is methyl (RS)-2-[4-(3-chloro-5-trifluoromethyl-2 -pyridyloxy)phenoxy]propionate;

K is 3-(5-tert-butyl-3-isoxazolyl)-4-hydroxy-1-methyl-2-imidazolidinone;

L is 2-(O-ethyloxime) of 2-butyryl-5-[2-(ethylthio)propyl]-3-hydroxy-2-cyclohexen-1-one;

M is ethyl 2-{p-[(6-chloro-2-benzoxazolyl)oxy]phenoxy}propionate;

N is ethyl o-{[(4-chloro-6-methoxy-2-pyrimidinyl)carbamoyl] sulfamoyl}benzoate;

O is 1-[(o-acetylphenyl)sulfamoyl]-3-(4,6-dimethoxy- 2-pyrimidinyl)urea;

P is 1-{[o-(cyclopropylcarbonyl)phenyl]sulfamoyl}-3-( 4,6-dimethoxy-2-pyrimidinyl)urea; and Q is methyl 2-(4-isopropyl-4-methyl-5-oxo-2-imidazolin-2-yl)nicotinate.

TABLE III

| Treatment | Rate (kg/ha) | % Growth Reduction |
|---|---|---|
| B | 0.0015 | 17 |
| B + A | 0.0015 + 0.50 | 28 |
| B | 0.003 | 38 |
| B + A | 0.003 + 0.50 | 40 |
| C | 0.0015 | 31 |
| C + A | 0.0015 + 0.50 | 11 |
| C | 0.003 | 34 |
| C + A | 0.003 + 0.50 | 14 |
| D | 0.006 | 31 |
| D + A | 0.006 + 0.50 | 17 |
| D | 0.012 | 36 |
| D + A | 0.012 + 0.50 | 21 |
| E | 0.025 | 75 |
| E + A | 0.025 + 0.50 | 78 |
| E | 0.05 | 78 |
| E + A | 0.05 + 0.50 | 80 |
| F | 0.006 | 14 |
| F + A | 0.006 + 0.50 | 4 |
| F | 0.012 | 34 |
| F + A | 0.012 + 0.50 | 23 |
| G | 0.012 | 35 |
| G + A | 0.012 + 0.50 | 24 |
| G | 0.025 | 36 |
| G + A | 0.025 + 0.50 | 27 |
| H | 0.012 | 46 |
| H + A | 0.012 + 0.50 | 34 |
| H | 0.025 | 70 |
| H + A | 0.025 + 0.50 | 75 |

TABLE III-continued

| Treatment | Rate (kg/ha) | % Growth Reduction |
|---|---|---|
| I | 0.10 | 3 |
| I + A | 0.10 + 0.50 | 0 |
| I | 0.25 | 47 |
| I + A | 0.25 + 0.50 | 37 |
| J | 0.012 | 60 |
| J + A | 0.012 + 0.50 | 64 |
| J | 0.025 | 59 |
| J + A | 0.025 + 0.50 | 62 |
| K | 0.05 | 9 |
| K + A | 0.05 + 0.50 | 4 |
| K | 0.10 | 15 |
| K + A | 0.10 + 0.50 | 29 |
| L | 0.025 | 13 |
| L + A | 0.025 + 0.50 | 12 |
| L | 0.05 | 54 |
| L + A | 0.05 + 0.50 | 28 |
| M | 0.006 | 63 |
| M + A | 0.006 + 0.50 | 46 |
| M | 0.012 | 54 |
| M + A | 0.012 + 0.50 | 62 |
| N | 0.025 | 78 |
| N + A | 0.025 + 0.50 | 77 |
| N | 0.05 | 78 |
| N + A | 0.05 + 0.50 | 80 |
| O | 0.012 | −5 |
| O + A | 0.012 + 0.50 | −11 |
| O | 0.025 | −8 |
| O + A | 0.025 + 0.50 | 0 |
| P | 0.012 | 14 |
| P + A | 0.012 + 0.50 | 6 |
| P | 0.025 | 29 |
| P + A | 0.025 + 0.50 | 3 |
| Q | 0.012 | 0 |
| Q + A | 0.012 + 0.50 | 4 |
| Q | 0.025 | 15 |
| Q + A | 0.025 + 0.50 | 7 |

EXAMPLE 21

Evaluation of the diammonium salt of 4-Carboxy-3,4 -dihydro-2H-1-benzopyran-4-acetic acid as a safener for oat injury from postemergence applications of herbicides Oat plants (Porter) approximately 4 to 5 inches tall are sprayed with a formulation of the appropriate herbicide, or a formulation of the appropriate herbicide mixed with a formulation of the diammonium salt of 4carboxy-3,4-dihydro-2H-1-benzopyran- 4-acetic acid. The herbicide and safener are diluted with water to provide the equivalent of 0.012 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table IV wherein

A is the diammonium salt of 4-carboxy-3,4-dihydro-2H-1-benzopyran-4-acetic acid;

C is 1-[(o-chlorophenyl)sulfonyl]-3-(4-methoxy-6 -methyl-S-triazin-2-yl)urea;

D is 1-[(o-acetylphenyl)sulfamoyl]-3-(4-methoxy-6-methyl-2-pyrimidinyl)urea;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

I is 3-{p-[(3,5-dichloro-2-pyridyl)oxy]phenoxy}-2-hydroxybutyronitrile ethyl carbonate;

J is methyl (RS)-2-[4-(3-chloro-5-trifluoromethyl-2-pyridyloxy)phenoxy]propionate;

O is 1-[(o-acetylphenyl)sulfamoyl]-3-(4,6-dimethoxy-2-pyrimidinyl)urea;

P is 1-{[o-(cyclopropylcarbonyl)phenyl]sulfamoyl}-3-(4,6-dimethoxy-2-pyrimidinyl)urea; and Q is methyl 2-(4-isopropyl-4-methyl-5-oxo-2-imidazolin-2-yl)nicotinate.

TABLE IV

| Treatment | Rate (kg/ha) | % Growth Reduction |
|---|---|---|
| C | 0.05 | 22 |
| C + A | 0.05 + 0.50 | 12 |
| C | 0.10 | 34 |
| C + A | 0.10 + 0.50 | 24 |
| D | 0.025 | 63 |
| D + A | 0.025 + 0.50 | 58 |
| D | 0.05 | 59 |
| D + A | 0.05 + 0.50 | 65 |
| F | 0.012 | 13 |
| F + A | 0.012 + 0.50 | −2 |
| F | 0.025 | 49 |
| F + A | 0.025 + 0.50 | 24 |
| G | 0.012 | 70 |
| G + A | 0.012 + 0.50 | 57 |
| G | 0.025 | 68 |
| G + A | 0.025 + 0.50 | 69 |
| H | 0.012 | 61 |
| H + A | 0.012.+ 0.50 | 41 |
| H | 0.025 | 67 |
| H + A | 0.025 + 0.50 | 69 |
| I | 0.25 | 3 |
| I + A | 0.25 + 0.50 | −2 |
| I | 0.50 | 20 |
| I + A | 0.50 + 0.50 | 3 |
| J | 0.012 | 51 |
| J + A | 0.012 + 0.50 | 47 |
| J | 0.025 | 54 |
| J + A | 0.025 + 0.50 | 57 |
| O | 0.25 | 37 |
| O + A | 0.25 + 0.50 | 8 |
| O | 0.50 | 47 |
| O + A | 0.50 + 0.50 | 32 |
| P | 0.012 | 13 |
| P + A | 0.012 + 0.50 | 6 |
| P | 0.025 | 20 |
| P + A | 0.025 + 0.50 | 11 |
| Q | 0.025 | 30 |
| Q + A | 0.025 + 0.50 | 28 |
| Q | 0.05 | 61 |
| Q + A | 0.05 + 0.50 | 40 |

EXAMPLE 22

Evaluation of the diammonium salt of 4-Carboxy-3,4-dihydro- 2H-1-benzopyran-4-acetic acid as a safener for spring wheat injury from postemergence applications of herbicides Spring wheat plants (Apollo) approximately 4 to 5 inches tall are sprayed with a formulation of the appropriate herbicide, or a formulation of the appropriate herbicide mixed with a formulation of the diammonium salt of 4-carboxy-3, 4-dihydro-2H-1-benzopyran- 4-acetic acid. The herbicide and safener are diluted with water to provide the equivalent of 0.012 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2–4 weeks after treatment, the tests are terminated and each pot is examined and rated by measuring the height of the foliage. The test results are averaged and expressed as a percent growth reduction compared to an untreated check, as described in example 18.

The results are summarized in Table V wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-S-methyl-S-triazin-2-yl)urea;

D is 1-[(o-acetylphenyl)sulfamoyl]-3-(4-methoxy-6-methyl-2-pyrimidinyl)urea;

E is 2-(4-isopropyl-4-methyl-5-oxo-2-imidazolin-2-yl)-5-methylnicotinic acid;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

J is methyl (RS)-2-[4-(3-chloro-5-trifluoromethyl-2-pyridyloxy)phenoxy]propionate;

M is ethyl 2-{p-[(6-chloro-2-benzoxazolyl)oxy]phenoxy} propionate; and

Q is methyl 2-(4-isopropyl-4-methyl-5-oxo-2-imidazolin-2-yl)nicotinate.

TABLE V

| Treatment | Rate (kg/ha) | % Growth Reduction |
|---|---|---|
| B | 0.075 | 66 |
| B + A | 0.075 +0.50 | 64 |
| B | 0.10 | 67 |
| B + A | 0.10 +0.50 | 62 |
| C | 0.05 | 26 |
| C + A | 0.05 +0.50 | 20 |
| C | 0.10 | 25 |
| C, + A | 0.10 +0.50 | 25 |
| D | 0.025 | 63 |
| D + A | 0.025 + 0.50 | 56 |
| D | 0.05 | 60 |
| D + A | 0.05 + 0.50 | 60 |
| E | 0.05 | 21 |
| E + A | 0.05 + 0.50 | 9 |
| E | 0.10 | 53 |
| E + A | 0.10 + 0.50 | 58 |
| F | 0.025 | 4 |
| F + A | 0.025 + 0.50 | −3 |
| F | 0.05 | 2 |
| F + A | 0.05 + 0.50 | 6 |
| G | 0.012 | 21 |
| G + A | 0.012 + 0.50 | 19 |
| G | 0.025 | 31 |
| G + A | 0.025 + 0.50 | 22 |
| H | 0.012 | 27 |
| H + A | 0.012 + 0.50 | 16 |
| H | 0.025 | 54 |
| H + A | 0.025 + 0.50 | 50 |

TABLE V-continued

| Treatment | Rate (kg/ha) | % Growth Reduction |
| --- | --- | --- |
| I | 0.012 | 40 |
| J + A | 0.012 + 0.50 | 18 |
| J | 0.025 | 49 |
| J + A | 0.025 + 0.50 | 47 |
| M | 0.025 | 6 |
| M + A | 0.025 + 0.50 | 1 |
| M | 0.05 | 13 |
| M + A | 0.05 + 0.50 | 10 |
| Q | 0.025 | 15 |
| Q + A | 0.025 + 0.50 | 6 |
| Q | 0.05 | 30 |
| Q + A | 0.05 + 0.50 | 15 |

EXAMPLE 23

Evaluation of the diammonium salt of 4-Carboxy-3,4-dihydro-2H-1-benzopyran-4-acetic acid as a safener for rice injury from postemergence applications of herbicides Rice plants (Tebonnet) approximately 4 to 5 inches tall are sprayed with a formulation of the appropriate herbicide, or a formulation of the appropriate herbicide mixed with a formulation of the diammonium salt of 4-carboxy-3,4-dihydro-2H-1-benzopyran- 4-acetic acid. The herbicide and safener are diluted with water to provide the equivalent of 0.0015 kg/ha to 0.250 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table VI wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-6-methyl-S-triazin-2-yl)urea;

D is 1-[(o-acetylphenyl)sulfamoyl]-3-(4-methoxy-6-methyl-2-pyrimidinyl)urea;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

J is methyl (RS)-2-[4-(3-chloro-5-trifluoromethyl-2-pyridyloxy)phenoxy]propionate;

K is 3-(5-tert-butyl-3-isoxazolyl)-4-hydroxy-1-methyl-2-imidazolidinone;

L is 2-(O-ethyloxime) of 2-butyryl-5-[2-(ethylthio)propyl]-3-hydroxy-2-cyclohexen-1-one;

M is ethyl 2-{p-[(6-chloro-2-benzoxazolyl)oxy]phenoxy}propionate;

N is ethyl o-{[(4-chloro-6-methoxy-2-pyrimidinyl)carbamoyl]sulfamoyl}benzoate;

P is 1-{o-(cyclopropylcarbonyl)phenyl]sulfamoyl}-3-(4,6-dimethoxy-2-pyrimidinyl)urea; and Q is methyl 2-(4-isopropyl-4-methyl-5-oxo-2-imidazolin-2-yl)nicotinate.

TABLE VI

| Treatment | Rate (kg/ha) | % Growth Reduction |
| --- | --- | --- |
| B | 0.0015 | 33 |
| B + A | 0.0015 + 0.50 | 35 |
| B | 0.003 | 65 |
| B + A | 0.003 + 0.50 | 42 |
| C | 0.0015 | 45 |
| C + A | 0.0015 + 0.50 | 35 |
| C | 0.003 | 42 |
| C + A | 0.003 + 0.50 | 56 |
| D | 0.05 | 40 |
| D + A | 0.05 + 0.50 | 35 |
| D | 0.10 | 49 |
| D + A | 0.10 + 0.50 | 40 |
| F | 0.003 | −3 |
| F + A | 0.003 + 0.50 | −6 |
| F | 0.006 | 5 |
| F + A | 0.006 + 0.50 | −3 |
| G | 0.012 | 26 |
| G + A | 0.012 + 0.50 | 12 |
| G | 0.025 | 32 |
| G + A | 0.025 + 0.50 | 60 |
| H | 0.012 | 47 |
| H + A | 0.012 + 0.50 | 43 |
| H | 0.025 | 57 |
| H + A | 0.025 + 0.50 | 61 |
| J | 0.012 | 24 |
| J + A | 0.012 + 0.50 | 22 |
| J | 0.025 | 45 |
| J + A | 0.025 + 0.50 | 39 |
| K | 0.05 | 50 |
| K + A | 0.05 + 0.50 | 47 |
| K | 0.10 | 49 |
| K + A | 0.10 + 0.50 | 51 |
| L | 0.025 | 12 |
| L + A | 0.025 + 0.50 | 3 |
| L | 0.05 | 41 |
| L + A | 0.05 + 0.50 | 16 |
| M | 0.006 | 19 |
| M + A | 0.006 + 0.50 | 10 |
| M | 0.012 | 22 |
| M + A | 0.012 + 0.50 | 22 |
| N | 0.025 | 66 |
| N + A | 0.025 + 0.50 | 66 |
| N | 0.05 | 63 |
| N + A | 0.05 + 0.50 | 59 |
| P | 0.012 | 20 |
| P + A | 0.012 + 0.50 | 1 |
| P | 0.025 | 7 |
| P + A | 0.025 + 0.50 | 2 |
| Q | 0.012 | 6 |
| Q + A | 0.012 + 0.50 | 15 |
| Q | 0.025 | 36 |
| Q + A | 0.025 + 0.50 | 31 |

EXAMPLE 24

Evaluation of the diammonium salt of 4-Carboxy-3,4-dihydro-2H-1-benzopyran-4-acetic acid as a safener for durum (spring) wheat injury from postemergence applications of herbicides Durum (spring) wheat plants (Wakooma) approximately 4 to 5 inches tall are sprayed with a formulation of the appropriate herbicide, or a formulation of the appropriate herbicide mixed with a formulation of the diammonium salt of 4-carboxy-3,4-dihydro2H-1-benzopyran- 4-acetic acid. The herbicide and safener are diluted with water to provide the equivalent of 0.003 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table VII wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-6-methyl-S-triazin-2-yl)urea;

D is 1-[(o-acetylphenyl)sulfamoyl]-3-(4-methoxy-6-methyl-2-pyrimidinyl)urea;

F is 5-ethyl-2-(4-isopropyl-4-methyl-5-oxo-2-imidazolin-2-yl)nicotinic acid;

G is 2-(4-isopropyl-4-methyl-5-oxo-2-imidazolin-2-yl)-3-quinolinecarboxylic acid;

H is isopropylammonium 2-(4-isopropyl-4-methyl-5-oxo-2-imidazolin-2-yl)nicotinate;

J is methyl (RS)-2-[4-(3-chloro-5-trifluoromethyl-2-pyridyloxy)phenoxy]propionate;

K is 3-(5-tert-butyl-3-isoxazolyl)-4-hydroxy-1-methyl-2-imidazolidinone;

L is 2-(O-ethyloxime) of 2-butyryl-5-[2-(ethylthio)propyl]-3-hydroxy-2-cyclohexen-1-one;

M is ethyl 2-{p-[(6-chloro-2-benzoxazolyl)oxy]phenoxy}propionate;

N is ethyl o-{[(4-chloro-6-methoxy-2-pyrimidinyl)carbamoyl] sulfamoyl}benzoate;

O is 1-[(o-acetylphenyl)sulfamoyl]-3-(4,6-dimethoxy-2-pyrimidinyl)urea; and

Q is methyl 2-(4-isopropyl-4-methyl-5-oxo-2-imidazolin-2-yl)nicotinate.

TABLE VII

| Treatment | Rate (kg/ha) | % Growth Reduction |
|---|---|---|
| B | 0.075 | 65 |
| B + A | 0.075 + 0.50 | 66 |
| B | 0.10 | 67 |
| B + A | 0.10 + 0.50 | 64 |
| C | 0.05 | 46 |
| C + A | 0.05 + 0.50 | 46 |
| C | 0.10 | 63 |
| C + A | 0.10 + 0.50 | 60 |
| D | 0.025 | 57 |
| D + A | 0.025 + 0.50 | 53 |
| D | 0.05 | 57 |
| D + A | 0.05 + 0.50 | 54 |
| F | 0.003 | 10 |
| F + A | 0.003 + 0.05 | 2 |
| F | 0.006 | 8 |
| F + A | 0.006 + 0.50 | 9 |
| G | 0.012 | 39 |
| G + A | 0.012 + 0.50 | 53 |
| G | 0.025 | 52 |
| G + A | 0.025 + 0.50 | 50 |
| H | 0.012 | 50 |
| H + A | 0.012 + 0.50 | 34 |
| H | 0.025 | 63 |

TABLE VII-continued

| Treatment | Rate (kg/ha) | % Growth Reduction |
|---|---|---|
| H + A | 0.025 + 0.50 | 60 |
| J | 0.012 | 50 |
| J + A | 0.012 + 0.50 | 17 |
| J | 0.025 | 62 |
| J + A | 0.025 + 0.50 | 45 |
| K | 0.05 | 10 |
| K + A | 0.05 + 0.50 | 5 |
| K | 0.10 | 28 |
| K + A | 0.10 + 0.50 | 15 |
| L | 0.10 | 17 |
| L + A | 0.10 + 0.50 | 19 |
| L | 0.25 | 52 |
| L + A | 0.25 + 0.50 | 54 |
| M | 0.025 | 54 |
| M + A | 0.025 + 0.50 | 43 |
| M | 0.05 | 56 |
| M + A | 0.05 + 0.50 | 61 |
| N | 0.025 | 68 |
| N + A | 0.025 + 0.50 | 67 |
| N | 0.05 | 68 |
| N + A | 0.05 + 0.50 | 71 |
| O | 0.25 | 27 |
| O + A | 0.25 + 0.50 | 25 |
| O | 0.50 | 42 |
| O + A | 0.50 + 0.50 | 33 |
| Q | 0.025 | 35 |
| Q + A | 0.025 + 0.50 | 43 |
| Q | 0.05 | 66 |
| Q + A | 0.05 + 0.50 | 51 |

EXAMPLE 25

Evaluation of the diammonium salt of 4-Carboxy-3,4-dihydro-2H-1-benzopyran-4-acetic acid as a safener for winter barley injury from postemergence applications of herbicides Winter barley plants (Marinka) approximately 4 to 5 inches tall are sprayed with a formulation of the appropriate herbicide, or a formulation of the appropriate herbicide mixed with a formulation of the diammonium salt of 4-carboxy-3,4-dihydro-2H-1-benzopyran-4-acetic acid. The herbicide and safener are diluted with water to provide the equivalent of 0.012 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in example 18.

The results are summarized in Table VIII wherein

A is the diammonium salt of 4-carboxy-3,4-dihydro-2H-1-benzopyran-4-acetic acid;

C is 1-[(o-chlorophenyl)sulfonyl]-3-(4-methoxy-6-methyl-S-triazin-2-yl)urea;

D is 1-[(o-acetylphenyl)sulfamoyl]-3-(4-methoxy-6-methyl-2-pyrimidinyl)urea;

E is 2-(4-isopropyl-4-methyl-5-oxo-2-imidazolin-2-yl)-5-methylnicotinic acid;

F is 5-ethyl-2-(4-isopropyl-4-methyl-5-oxo-2-imidazolin-2-yl)nicotinic acid;

H is isopropylammonium 2-(4-isopropyl-4-methyl-5-oxo-2-imidazolin-2-yl)nicotinate;

I is 3-{p-[(3,5-dichloro-2-pyridyl)oxy]phenoxy}-2-hydroxybutyronitrile ethyl carbonate;

J is methyl (RS)-2-[4-(3-chloro-5-trifluoromethyl-2-pyridyloxy)phenoxy]propionate;

K is 3-(5-tert-butyl-3-isoxazolyl)-4-hydroxy-1-methyl-2-imidazolidinone;

L is 2-(O-ethyloxime) of 2-butyryl-5-[2-(ethylthio)propyl]-3-hydroxy-2-cyclohexen-1-one;

O is 1-[(o-acetylphenyl)sulfamoyl]-3-(4,6-dimethoxy-2-pyrimidinyl)urea;

P is 1-{[o-(cyclopropylcarbonyl)phenyl]sulfamoyl}-3-(4,6-dimethoxy-2-pyrimidinyl)urea; and Q is methyl 2-(4-isopropyl-4-methyl-5-oxo-2-imidazolin-2-yl)nicotinate.

TABLE VIII

| Treatment | Rate (kg/ha) | % Growth Reduction |
| --- | --- | --- |
| C | 0.05 | 4 |
| C + A | 0.05 + 0.50 | 13 |
| C | 0.10 | 34 |
| C + A | 0.10 + 0.50 | 16 |
| D | 0.025 | 60 |
| D + A | 0.025 + 0.50 | 54 |
| D | 0.05 | 61 |
| D + A | 0.05 + 0.50 | 61 |
| E | 0.05 | 61 |
| E + A | 0.05 + 0.50 | 56 |
| E | 0.075 | 61 |
| E + A | 0.075 + 0.50 | 61 |
| F | 0.05 | 37 |
| F + A | 0.05 + 0.50 | 20 |
| F | 0.10 | 53 |
| F + A | 0.10 + 0.50 | 56 |
| H | 0.012 | 40 |
| H + A | 0.012 + 0.50 | 31 |
| H | 0.025 | 60 |
| H + A | 0.025 + 0.50 | 55 |
| I | 0.25 | 5 |
| I + A | 0.25 + 0.50 | −10 |
| I | 0.50 | −7 |
| I + A | 0.50 + 0.50 | −11 |
| J | 0.012 | 56 |
| J + A | 0.012 + 0.50 | 28 |
| J | 0.025 | 58 |
| J + A | 0.025 + 0.50 | 59 |
| K | 0.05 | 5 |
| K + A | 0.05 + 0.50 | 0 |
| K | 0.10 | 18 |
| K + A | 0.10 + 0.50 | 22 |
| L | 0.10 | 12 |
| L + A | 0.10 + 0.50 | 16 |
| L | 0.25 | 36 |
| L + A | 0.25 + 0.50 | 31 |
| O | 0.25 | 27 |
| O + A | 0.25 + 0.50 | 25 |
| O | 0.50 | 42 |
| O + A | 0.50 + 0.50 | 33 |
| P | 0.012 | 13 |
| P + A | 0.012 + 0.50 | 9 |
| P | 0.025 | 14 |
| P + A | 0.025 + 0.50 | 9 |
| Q | 0.025 | 21 |
| Q + A | 0.025 + 0.50 | 9 |
| Q | 0.50 | 33 |
| Q + A | 0.50 + 0.50 | 28 |

EXAMPLE 26

Evaluation of the diammonium salt of 4-Carboxy-3,4-dihydro-2H-1-benzopyran-4-acetic acid as a safener for cotton injury from postemergence applications of herbicides Cotton plants (825) at the cotyledon stage are sprayed with a formulation of the appropriate herbicide, or a formulation of the appropriate herbicide mixed with a formulation of the diammonium salt of 4-carboxy-3,4-dihydro-2H-1-benzopyran-4-acetic acid. The herbicide and safener are diluted with water to provide the equivalent of 0.0015 kg/ha to 0.10 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and the foliage is clipped and dried. The dry clipping weight results are averaged and expressed as a percent growth reduction compared to an untreated check, using the following formula:

$$\% \text{ Growth Reduction} = 100 - \left[ \frac{\text{Dry Weight of Treated Plants}}{\text{Dry Weight of Untreated Plants}} \times 100 \right]$$

The results are summarized in Table IX wherein

A is the diammonium salt of 4-carboxy-3,4-dihydro-2H-1-benzopyran-4-acetic acid;

B is methyl o-{{3-[4,6-bis(difluoromethoxy)-2-pyrimidinyl]ureido}sulfonyl}benzoate;

C is 1-[(o-chlorophenyl)sulfonyl]-3-(4-methoxy-6-methyl-S-triazin-2-yl)urea;

E is 2-(4-isopropyl-4-methyl-5-oxo-2-imidazolin-2-yl)-5-methylnicotinic acid;

F is 5-ethyl-2-(4-isopropyl-4-methyl-5-oxo-2-imidazolin-2-yl)nicotinic acid;

H is isopropylammonium 2-(4-isopropyl-4-methyl-5-oxo-2-imidazolin-2-yl)nicotinate;

J is methyl (RS)-2-[4-(3-chloro-5-trifluoromethyl-2-pyridyloxy)phenoxy]propionate; and Q is methyl 2-(4-isopropyl-4-methyl-5-oxo-2-imidazolin-2-yl)nicotinate.

TABLE IX

| Treatment | Rate (kg/ha) | % Growth Reduction |
| --- | --- | --- |
| B | 0.0015 | 23 |
| B + A | 0.0015 + 0.50 | 4 |
| B | 0.003 | 4 |
| B + A | 0.003 + 0.50 | 25 |
| C | 0.0015 | 93 |
| C + A | 0.0015 + 0.50 | 77 |
| C | 0.003 | 92 |
| C + A | 0.003 + 0.50 | 89 |
| E | 0.05 | 58 |
| E + A | 0.05 + 0.50 | 51 |
| E | 0.075 | 57 |
| E + A | 0.075 + 0.50 | 55 |
| F | 0.05 | 76 |
| F + A | 0.05 + 0.50 | 56 |
| F | 0.10 | 72 |
| F + A | 0.10 + 0.50 | 82 |
| H | 0.012 | 60 |
| H + A | 0.012 + 0.50 | 18 |
| H | 0.025 | 73 |

TABLE IX-continued

| Treatment | Rate (kg/ha) | % Growth Reduction |
|---|---|---|
| H + A | 0.025 + 0.50 | 51 |
| J | 0.012 | 23 |
| J + A | 0.012 + 0.50 | 6 |
| J | 0.025 | 9 |
| J + A | 0.025 + 0.50 | 3 |
| Q | 0.012 | 60 |
| Q + A | 0.012 + 0.50 | 61 |
| Q | 0.025 | 78 |
| Q + A | 0.025 + 0.50 | 76 |

EXAMPLE 27

Evaluation of
4-Carboxy-3,4-dihydro-2H-1-benzopyran- 4-acetic acid applied as a seed treatment for injury to corn caused by postemergence applications of herbicides Corn seeds (Pioneer 3475) are treated with the safener 4-carboxy-3,4-dihydro-2H-1-benzopyran-4 -acetic acid by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of corn seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 to 3 leaf stage, the corn plants are sprayed with a herbicide solution. The herbicide spray solution is diluted with water to provide the equivalent of 0.006 to 0.05 kg/ha of herbicide to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in example 18.

The results are summarized in Table X wherein
A is 4-carboxy-3,4-dihydro-2H-1-benzopyran-4-acetic acid;
F is 5-ethyl-2-(4-isopropyl-4-methyl-5-oxo-2-imidazolin-2-yl)nicotinic acid;
E is 2-(4-isopropyl-4-methyl-5-oxo-2-imidazolin-2 -yl)-5-methylnicotinic acid; and
H is isopropylammonium 2-(4-isopropyl-4-methyl-5-oxo-2-imidazolin-2-yl)nicotinate.

TABLE X

| Treatment | Rate (kg/ha) | (mg/g of seed) | % Growth Reduction |
|---|---|---|---|
| F | 0.05 | | 60 |
| F + A | 0.05 | 0.25 | 52 |
| F + A | 0.05 | 0.50 | 52 |
| F + A | 0.05 | 1.0 | 40 |
| F + A | 0.05 | 2.0 | 35 |
| F + A | 0.05 | 4.0 | 29 |
| E | 0.025 | | 35 |
| E + A | 0.025 | 0.25 | 10 |
| E + A | 0.025 | 0.50 | 31 |
| E + A | 0.025 | 1.0 | 20 |
| E + A | 0.025 | 2.0 | 11 |
| E + A | 0.025 | 4.0 | −5 |
| E | 0.05 | | 64 |
| E + A | 0.05 | 0.25 | 48 |
| E + A | 0.05 | 0.50 | 57 |
| E + A | 0.05 | 1.0 | 65 |
| E + A | 0.05 | 2.0 | 46 |
| E + A | 0.05 | 4.0 | 11 |
| H | 0.006 | | 12 |
| H + A | 0.006 | 0.25 | 6 |
| H + A | 0.006 | 0.50 | 3 |
| H + A | 0.006 | 1.0 | 2 |
| H + A | 0.006 | 2.0 | −6 |
| H + A | 0.006 | 4.0 | −13 |
| H | 0.012 | | 42 |
| H + A | 0.012 | 0.25 | 57 |
| H + A | 0.012 | 0.50 | 60 |
| H + A | 0.012 | 1.0 | 47 |
| H + A | 0.012 | 2.0 | 42 |
| H + A | 0.012 | 4.0 | 23 |

EXAMPLE 28

Evaluation of
4-Carboxy-3,4-dihydro-2H-1-benzopyran- 4-acetic acid applied as a seed treatment for injury to barley caused by postemergence applications of herbicides Barley seeds (Volga) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of barley seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 1 to 2 leaf stage, the barley plants are sprayed with a herbicide solution. The herbicide spray solution is diluted with water to provide the equivalent of 0.006 to 0.1 kg/ha of herbicide to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in example 18.

The results are summarized in Table XI wherein
A is 4-carboxy-3,4-dihydro-2H-1-benzopyran-4-acetic acid;
H is isopropylammonium 2-(4-isopropyl-4-methyl-5 -oxo-2-imidazolin-2-yl)nicotinate; and M is ethyl 2-{p-[(6-chloro-2-benzoxazolyl)oxy]phenoxy} propionate.

TABLE XI

| Treatment | Rate (kg/ha) | (mg/g of seed) | % Growth Reduction |
|---|---|---|---|
| H | 0.006 | | 31 |
| H + A | 0.006 | 0.25 | 28 |
| H + A | 0.006 | 0.50 | 16 |
| H + A | 0.006 | 1.0 | 21 |
| H + A | 0.006 | 2.0 | 22 |
| H + A | 0.006 | 4.0 | 22 |
| H | 0.012 | | 65 |
| H + A | 0.012 | 0.25 | 68 |
| H + A | 0.012 | 0.50 | 64 |
| H + A | 0.012 | 1.0 | 67 |
| H + A | 0.012 | 2.0 | 64 |
| H + A | 0.012 | 4.0 | 69 |
| H | 0.025 | | 66 |
| H + A | 0.025 | 0.25 | 66 |
| H + A | 0.025 | 0.50 | 65 |
| H + A | 0.025 | 1.0 | 63 |
| H + A | 0.025 | 2.0 | 66 |
| H + A | 0.025 | 4.0 | 67 |
| M | 0.025 | | −1 |
| M + A | 0.025 | 0.25 | −5 |
| M + A | 0.025 | 0.50 | −4 |
| M + A | 0.025 | 1.0 | −6 |
| M + A | 0.025 | 2.0 | −4 |
| M | 0.050 | | 8 |
| M + A | 0.050 | 0.25 | 1 |
| M + A | 0.050 | 0.50 | 3 |
| M + A | 0.050 | 1.0 | 3 |
| M + A | 0.050 | 2.0 | 3 |
| M | 0.10 | | 20 |
| M + A | 0.10 | 0.25 | 8 |
| M + A | 0.10 | 0.50 | 11 |
| M + A | 0.10 | 1.0 | 11 |
| M + A | 0.10 | 2.0 | 2 |

EXAMPLE 29

Evaluation of 4-Carboxy-3,4-dihydro-2H-1-benzopyran- 4-acetic acid applied as a seed treatment for injury to sorghum caused by postemergence application of 2-(4 -isopropyl-4-methyl-5-oxo-2-imidazolin-2-yl)-3-quinolinecarboxylic acid Sorghum seeds (NC 271) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of sorghum seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 to 3 leaf stage, the sorghum plants are sprayed with a 2-(4-isopropyl-4-methyl-5-oxo-2-imidazolin-2 -yl)-3-quinolinecarboxylic acid formulation. The 2-(4-isopropyl-4-methyl-5-oxo-2-imidazolin-2-yl)-3-quinolinecarboxylic acid spray formulation is diluted with water to provide the equivalent of 0.01 to 0.025 kg/ha of 2-(4-isopropyl-4-methyl-5-oxo-2-imidazolin-2-yl)-3 -quinolinecarboxylic acid to the foliage when applied through a spray nozzle operating at 40 psi for a predetermined time. The 2-(4-isopropyl-4-methyl-5 -oxo-2-imidazolin-2-yl)-3-quinolinecarboxylic acid spray formulation contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in example 18.

The results are summarized in Table XII wherein
A is 4-carboxy-3,4-dihydro-2H-1-benzopyran-4-acetic acid; and
G is 2-(4-isopropyl-4-methyl-5-oxo-2-imidazolin-2-yl)-3-quinolinecarboxylic acid.

TABLE XII

| Treatment | Rate (kg/ha) | (mg/g of seed) | % Growth Reduction |
|---|---|---|---|
| G | 0.01 | | 17 |
| G + A | 0.01 | 0.25 | 15 |
| G + A | 0.01 | 0.50 | 7 |
| G + A | 0.01 | 1.0 | −2 |
| G + A | 0.01 | 2.0 | −1 |
| G + A | 0.01 | 4.0 | −14 |
| G | 0.025 | | 30 |
| G + A | 0.025 | 0.25 | 41 |
| G + A | 0.025 | 0.50 | 38 |
| G + A | 0.025 | 1.0 | 45 |
| G + A | 0.025 | 2.0 | 16 |
| G + A | 0.025 | 4.0 | 15 |

EXAMPLE 30

Evaluation of 4-Carboxy-3,4-dihydro-2H-1-benzopyran-4-acetic acid applied as a seed treatment for injury to oats caused by postemergence application of methyl 2-(4-isopropyl-4-methyl-5-oxo-2-imidazolin-2-yl)-nicotinate Tame oat seeds (Porter) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of oat seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 leaf stage, the oat plants are sprayed with a methyl 2-(4-isopropyl-4-methyl-5-oxo-2-imidazolin-2 -yl)nicotinate solution. The methyl 2-(4-isopropyl-4 -methyl-5-oxo-2-imidazolin-2-yl)nicotinate spray solution is diluted with water to provide the equivalent of 0.025 to 0.05 kg/ha of methyl 2-(4-isopropyl-4-methyl- 5-oxo-2-imidazolin-2-yl)nicotinate to the foliage when applied through a spray nozzle operating at 40 psi for a predetermined time. The methyl 2-(4-isopropyl-4 -methyl-5-oxo-2-imidazolin-2-yl)nicotinate spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in example 18.

The results are summarized in Table XIII wherein
A is 4-carboxy-3,4-dihydro-2H-1-benzopyran-4-acetic acid; and
Q is methyl 2-(4-isopropyl-4-methyl-5-oxo-2-imidazolin-2-yl)nicotinate.

TABLE XIII

| Treatment | Rate (kg/ha) | (mg/g of seed) | % Growth Reduction |
|---|---|---|---|
| Q | 0.025 | | 41 |
| Q + A | 0.025 | 0.25 | 28 |
| Q + A | 0.025 | 0.50 | 17 |
| Q + A | 0.025 | 1.0 | 31 |
| Q + A | 0.025 | 2.0 | 30 |
| Q + A | 0.025 | 4.0 | 28 |
| Q | 0.05 | | 50 |
| Q + A | 0.05 | 0.25 | 46 |
| Q + A | 0.05 | 0.50 | 43 |
| Q + A | 0.05 | 1.0 | 45 |
| Q + A | 0.05 | 2.0 | 44 |
| Q + A | 0.05 | 4.0 | 53 |

EXAMPLE 31

Evaluation of 4-Carboxy-3,4-dihydro-2H-1-benzopyran- 4-acetic acid applied as a seed treatment for injury to rice caused by postemergence application of 2-(4-isopropyl-4-methyl-5-oxo-2-imidazolin-2-yl)-3-quinolinecarboxlic acid Rice seeds (Tebonnet) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 62.5 µL to 1.0 mL are made up to 1 mL with an acetone:dimethylformamide (10:1) mixture, added to 10 g of rice seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 1 to 2 leaf stage, the rice plants are sprayed with a 2-(4-isopropyl-4-methyl-5-oxo-2-imidazolin-2-yl)-3 -quinolinecarboxylic acid formulation. The 2-(4-isopropyl- 4-methyl-5-oxo-2-imidazolin-2-yl)-3-quinolinecarboxylic acid spray formulation is diluted with water to provide the equivalent of 0.01 to 0.025 kg/ha of 2-(4-isopropyl-4-methyl-5-oxo-2-imidazolin-2-yl)-3 -quinolinecarboxylic acid to the foliage when applied through a spray nozzle operating at 40 psi for a predetermined time. The 2-(4-isopropyl-4-methyl-5-oxo-2-imidazolin-2-yl)-3-quinolinecarboxylic acid spray formulation contains 0.25% of the spray adjuvant ORTHO X-77, a non-ionic wetting agent containing alkylaryl polyoxyethylene, glycols, free fatty acids and isopropanol, manfactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 18.

The results are summarized in Table XIV wherein
A is 4-carboxy-3,4-dihydro-2H-1-benzopyran-4-acetic acid; and
G is 2-(4-isopropyl-4-methyl-5-oxo-2-imidazolin-2-yl)-3-quinolinecarboxylic acid.

TABLE XIV

| Treatment | Rate (kg/ha) | (mg/g of seed) | % Growth Reduction |
|---|---|---|---|
| G | 0.01 | | 24 |
| G + A | 0.01 | 0.25 | 4 |
| G + A | 0.01 | 0.50 | −5 |
| G + A | 0.01 | 1.0 | −3 |
| G + A | 0.01 | 2.0 | −9 |
| G + A | 0.01 | 4.0 | −6 |
| G | 0.025 | | 49 |
| G + A | 0.025 | 0.25 | 59 |
| G + A | 0.025 | 0.50 | 40 |
| G + A | 0.025 | 1.0 | 49 |
| G + A | 0.025 | 2.0 | 41 |
| G + A | 0.025 | 4.0 | 37 |

EXAMPLE 32

Evaluation of 4-Carboxy-3,4-dihydro-2H-1-benzopyran- 4-acetic acid applied as a seed treatment for injury to corn caused by preemergence applications of herbicides Corn seeds (Pioneer 3475) are treated with the safener 4-carboxy-3,4-dihydro-2H-1-benzopyran-4 -acetic acid by first making a stock solution of 100 mg of the safener in 2.5 mL of an acetone:dimethylformamide (5:1) mixture. Aliquots of the stock solution ranging from 62.5 µL to 1.0. mL are made up to 1 mL with an acetone:dimethylformamide (10:1) mixture, added to 10 g of corn seed and shaken thoroughly to provide seed treatment rates equivalent to 0.25 to 4.0 mg of safener per gram of seed. Seeds are dried and planted in soil. The soil surface is moistened and sprayed preemergence with a herbicide solution. The herbicide spray solution is diluted with water to provide the equivalent of 0.032 to 4.0 kg/ha of herbicide to the soil surface when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in example 18.

The results are summarized in Table XV wherein
A is 4-carboxy-3,4-dihydro-2H-1-benzopyran-4-acetic acid;
F is 5-ethyl-2-(4-isopropyl-4-methyl-5-oxo-2 -imidazolin-2-yl)nicotinic acid;
G is 2-(4-isopropyl-4-methyl-5-oxo-2-imidazolin-2 -yl)-3-quinolinecarboxylic acid; and R is 2-chloro-6'-ethyl-N-(2-methoxy-1-methylethyl)-o-acetotoluidide; and
S is N-(1-ethylpropyl)-3,4-dimethyl-2,6-dinitrobenzenamine.

TABLE XV

| Treatment | Rate (kg/ha) | (mg/g of seed) | % Growth Reduction |
|---|---|---|---|
| F | 0.1 | | 79 |
| F + A | 0.1 | 0.25 | 53 |
| F + A | 0.1 | 0.50 | 62 |
| F + A | 0.1 | 1.0 | 55 |
| F + A | 0.1 | 2.0 | 50 |
| F + A | 0.1 | 4.0 | 39 |
| G | 0.032 | | 74 |
| G + A | 0.032 | 0.25 | 71 |
| G + A | 0.032 | 0.50 | 82 |
| G + A | 0.032 | 1.0 | 71 |
| G + A | 0.032 | 2.0 | 67 |
| G + A | 0.032 | 4.0 | 38 |
| R | 2.0 | | 38 |
| R + A | 2.0 | 0.25 | 25 |
| R + A | 2.0 | 0.50 | 2 |
| R + A | 2.0 | 1.0 | −1 |
| R + A | 2.0 | 2.0 | −8 |
| R + A | 2.0 | 4.0 | −4 |
| R | 4.0 | | 53 |
| R + A | 4.0 | 0.25 | 35 |
| R + A | 4.0 | 0.50 | 23 |
| R + A | 4.0 | 1.0 | 16 |
| R + A | 4.0 | 2.0 | 8 |
| R + A | 4.0 | 4.0 | 12 |
| S | 2.5 | | 20 |
| S + A | 2.5 | 0.25 | 18 |
| s + A | 2.5 | 0.50 | 3 |
| S + A | 2.5 | 1.0 | 7 |
| S + A | 2.5 | 2.0 | 15 |

EXAMPLE 33

Evaluation of
4-Carboxy-3,4-dihydro-2H-1-benzopyran- 4-acetic
acid applied as a seed treatment for injury to oats
caused by preemergence applications of herbicides Tame oat seeds (Porter) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 25.0 µL to 0.5 mL are made up to 1 mL with an acetone:dimethylformamide (10:1) mixture, added to 10 g of seed and shaken thoroughly to provide seed treatment rates equivalent to 0.10 to 2.0 mg of safener per gram of seed. Seeds are dried and planted in soil. The soil surface is moistened and sprayed preemergence with a herbicide solution. The herbicide spray solution is diluted with water to provide the equivalent of 0.50 to 2.0 kg/ha of herbicide to the soil surface when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in example 18.

The results are summarized in Table XVI wherein
A is 4-carboxy-3,4-dihydro-2H-1-benzopyran-4-acetic acid;
R is 2-chloro-6'-ethyl-N-(2-methoxy-1-methylethyl)-o-acetotoluidide; and
T is ethyl dipropylthiolcarbamate.

TABLE XVI

| Treatment | Rate (kg/ha) | (mg/g of seed) | % Growth Reduction |
|---|---|---|---|
| R | 1.0 | | 34 |
| R + A | 1.0 | 0.10 | 40 |
| R + A | 1.0 | 0.25 | 40 |
| R + A | 1.0 | 0.50 | 40 |
| R + A | 1.0 | 1.00 | 38 |
| R + A | 1.0 | 2.00 | 26 |
| R | 2.0 | | 69 |
| R + A | 2.0 | 0.10 | 57 |
| R + A | 2.0 | 0.25 | 44 |
| R + A | 2.0 | 0.50 | 54 |
| R + A | 2.o | 1.00 | 50 |
| R + A | 2.0 | 2.00 | 42 |
| T | 0.5 | | 18 |
| T + A | 0.5 | 0.10 | 20 |
| T + A | 0.5 | 0.25 | 8 |
| T + A | 0.5 | 0.50 | 15 |
| T + A | 0.5 | 1.00 | 10 |
| T + A | 0.5 | 2.00 | −7 |
| T | 1.0 | | 61 |
| T + A | 1.0 | 0.10 | 74 |
| T + A | 1.0 | 0.50 | 67 |
| T + A | 1.0 | 1.00 | 55 |
| T + A | 1.0 | 2.00 | 49 |

EXAMPLE 34

Evaluation of
4-Carboxy-3,4-dihydro-2H-1-benzopyran- 4-acetic
acid applied as a seed treatment for injury to wheat
caused by preemergence application of 2-chloro-
6'-ethyl-N-(2-methoxy-1-methylethyl)-o-acetotoluidide Wheat seeds (Wakooma) are treated with the safener 4-carboxy-3,4-dihydro-2H-1-benzopyran-4-acetic acid by first making a stock solution of 100 mg of the safener in 2.5 mL of an acetone:dimethylformamide (5:1) mixture. Aliquots of the stock solution ranging from 25.0 µL to 0.5 mL are made up to 1 mL with an acetone:dimethylformamide (10:1) mixture, added to 10 g of wheat seed and shaken thoroughly to provide seed treatment rates equivalent to 0.10 to 2.0 mg of safener per gram of seed. Seeds are dried and planted in soil. The soil surface is moistened and sprayed preemergence with a 2-chloro-6'-ethyl-N-(2-methoxy-1-methylethyl)-o-acetotoluidide solution. The 2-chloro-6'-ethyl-N-(2 -methoxy-1-methylethyl)-o-acetotoluidide spray solution is diluted with water to provide the equivalent of 0.30 to 0.60 kg/ha of 2-chloro-6'-ethyl-N-(2-methoxy- 1-methylethyl)-o-acetotoluidide to the soil surface when applied through a spray nozzle operating at 40 psi for a predetermined time. The 2-chloro-6'-ethyl-N-(2 -methoxy-1-methylethyl)-o-acetotoluidide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in example 18.

The results are summarized in Table XVII wherein
A is 4-carboxy-3,4-dihydro-2H-1-benzopyran-4-acetic acid; and
R is 2-chloro-6'-ethyl-N-(2-methoxy-1-methylethyl)-o-acetotoluidide.

TABLE XVII

| Treatment | Rate (kg/ha) | (mg/g of seed) | % Growth Reduction |
|---|---|---|---|
| R | 0.30 | | 64 |
| R + A | 0.30 | 0.10 | 70 |
| R + A | 0.30 | 0.25 | 58 |
| R + A | 0.30 | 0.50 | 62 |
| R + A | 0.30 | 1.00 | 55 |
| R + A | 0.30 | 2.00 | 38 |
| R | 0.60 | | 75 |
| R + A | 0.60 | 0.10 | 88 |
| R + A | 0.60 | 0.25 | 77 |
| R + A | 0.60 | 0.50 | 80 |
| R + A | 0.60 | 1.00 | 76 |
| R + A | 0.60 | 2.00 | 63 |

EXAMPLE 35

Evaluation of 4-carboxy-3,4-dihydro-2H-1-benzopyran-4-acetic acid applied as a seed treatment for injury to corn caused by pre-plant incorporation of herbicides Three inch square pots are filled with 150 mL of Sassafras soil containing 17% sand and sprayed with a herbicide solution. The herbicide spray solution is diluted with water to provide the equivalent of 1.0 to 4.0 kg/ha of herbicide to the soil surface when applied through a spray nozzle operating at 40 psi for a predetermined time. After the soil is sprayed, it is poured into a plastic basin and mixed. The pots are refilled with 100 mL of the treated soil. Corn seeds (Pioneer 3475) are treated with the safener 4-carboxy-3,4-dihydro-2H-1-benzopyran-4-acetic acid according to the procedure described in example 27, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in example 18.

The results are summarized in Table XVIII wherein
A is 4-carboxy-3,4-dihydro-2H-1-benzopyran-4-acetic acid;
R is 2-chloro-6'-ethyl-N-(2-methoxy-1-methylethyl)-o-acetotoluidide; and
S is N-(1-ethylpropyl)-3,4-dimethyl-2,6-dinitrobenzenamine.

TABLE XVIII

| Treatment | Rate (kg/ha) | (mg/g of seed) | % Growth Reduction |
|---|---|---|---|
| R | 2.0 | | 21 |
| R + A | 2.0 | 0.10 | 13 |
| R + A | 2.0 | 0.25 | −5 |

TABLE XVIII-continued

| Treatment | Rate (kg/ha) | (mg/g of seed) | % Growth Reduction |
|---|---|---|---|
| R + A | 2.0 | 0.50 | 0 |
| R + A | 2.0 | 1.00 | 2 |
| R + A | 2.0 | 2.00 | 16 |
| R | 4.0 | | 38 |
| R + A | 4.0 | 0.10 | 14 |
| R + A | 4.0 | 0.25 | 17 |
| R + A | 4.0 | 0.50 | 10 |
| R + A | 4.0 | 1.00 | 6 |
| R + A | 4.0 | 2.00 | 3 |
| S | 1.0 | | 18 |
| S + A | 1.0 | 0.10 | −10 |
| S + A | 1.0 | 0.25 | −17 |
| S + A | 1.0 | 0.50 | −10 |
| S + A | 1.0 | 1.0 | −11 |
| S + A | 1.0 | 2.0 | −6 |
| S | 2.0 | | 26 |
| S + A | 2.0 | 0.10 | 23 |
| S + A | 2.0 | 0.25 | 2 |
| S + A | 2.0 | 0.50 | 6 |
| S + A | 2.0 | 1.0 | 6 |
| S + A | 2.0 | 2.0 | 8 |

EXAMPLE 36

Evaluation of 4-carboxy-3,4-dihydro-2H-1-benzopyran-4-acetic acid applied as a seed treatment for injury to barley caused by pre-plant incorporation of herbicides Three inch square pots are filled with 150 mL of Sassafras soil containing 17% sand and sprayed with a herbicide solution. The herbicide spray solution is diluted with water to provide the equivalent of 0.50 to 4.0 kg/ha of herbicide to the soil surface when applied through a spray nozzle operating at 40 psi for a predetermined time. After the soil is sprayed, it is poured into a plastic basin and mixed. The pots are refilled with 100 mL of the treated soil. Barley seeds (Volga) are treated with the safener 4-carboxy-3,4-dihydro-2H-1-benzopyran-4-acetic acid according to the procedure described in example 28, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in example 18.

The results are summarized in Table XIX wherein
A is 4-carboxy-3,4-dihydro-2H-1-benzopyran-4-acetic acid;
R is 2-chloro-6'-ethyl-N-(2-methoxy-1-methylethyl)-o-acetotoluidide; and
T is ethyl dipropylthiolcarbamate.

TABLE XIX

| Treatment | Rate (kg/ha) | (mg/g of seed) | % Growth Reduction |
|---|---|---|---|
| R | 2.0 | | 54 |
| R + A | 2.0 | 0.10 | 61 |
| R + A | 2.0 | 0.25 | 74 |
| R + A | 2.0 | 0.50 | 56 |
| R + A | 2.0 | 1.00 | 49 |
| R + A | 2.0 | 2.00 | 47 |

TABLE XIX-continued

| Treatment | Rate (kg/ha) | (mg/g of seed) | % Growth Reduction |
|---|---|---|---|
| R | 4.0 | | 72 |
| R + A | 4.0 | 0.10 | 81 |
| R + A | 4.0 | 0.25 | 71 |
| R + A | 4.0 | 0.50 | 71 |
| R + A | 4.0 | 1.00 | 65 |
| R + A | 4.0 | 2.00 | 63 |
| T | 0.5 | | 50 |
| T + A | 0.5 | 0.10 | 27 |
| T + A | 0.5 | 0.25 | 42 |
| T + A | 0.5 | 0.50 | 16 |
| T + A | 0.5 | 1.00 | 20 |
| T + A | 0.5 | 2.00 | 31 |
| T | 1.0 | | 86 |
| T + A | 1.0 | 0.10 | 96 |
| T + A | 1.0 | 0.25 | 38 |
| T + A | 1.0 | 0.50 | 37 |
| T + A | 1.0 | 1.00 | 47 |
| T + A | 1.0 | 2.00 | 31 |

EXAMPLE 37

Evaluation of 4-carboxy-3,4-dihydro,2H-1-benzopyran- 4-acetic acid applied as a seed treatment for injury to oats caused by pre-plant incorporation of herbicides Three inch square pots are filled with 150 mL of Sassafras soil containing 17% sand and sprayed with a herbicide solution. The herbicide spray solution is diluted with water to provide the equivalent of 0.125 to 3.0 kg/ha of herbicide to the soil surface when applied through a spray nozzle operating at 40 psi for a predetermined time. After the soil is sprayed, it is poured into a plastic basin and mixed. The pots are refilled with 100 mL of the treated soil. Oat seeds (Porter) are treated with the safener 4-carboxy-3,4 -dihydro-2H-1-benzopyran-4-acetic acid according to the procedure described in example 32, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in example 18.

The results are summarized in Table XX wherein
A is 4-carboxy-3,4-dihydro-2H-1-benzopyran-4-acetic acid;
R is 2-chloro-6'-ethyl-N-(2-methoxy-1-methylethyl)-o-acetotoluidide; and
T is ethyl dipropylthiolcarbamate.

TABLE XX

| Treatment | Rate (kg/ha) | (mg/g of seed) | % Growth Reduction |
|---|---|---|---|
| R | 1.5 | | 70 |
| R + A | 1.5 | 0.10 | 73 |
| R + A | 1.5 | 0.25 | 51 |
| R + A | 1.5 | 0.50 | 46 |
| R + A | 1.5 | 1.00 | 58 |
| R + A | 1.5 | 2.00 | 36 |
| R | 3.0 | | 86 |
| R + A | 3.0 | 0.10 | 86 |
| R + A | 3.0 | 0.25 | 84 |

TABLE XX-continued

| Treatment | Rate (kg/ha) | (mg/g of seed) | % Growth Reduction |
|---|---|---|---|
| R + A | 3.0 | 0.50 | 80 |
| R + A | 3.0 | 1.00 | 76 |
| R + A | 3.0 | 2.00 | 72 |
| T | 0.125 | | 45 |
| T + A | 0.125 | 0.10 | 27 |
| T + A | 0.125 | 0.25 | 28 |
| T + A | 0.125 | 0.50 | 32 |
| T + A | 0.125 | 1.00 | 32 |
| T + A | 0.125 | 2.00 | 20 |
| T | 0.25 | | 88 |
| T + A | 0.25 | 0.10 | 80 |
| T + A | 0.25 | 0.25 | 71 |
| T + A | 0.25 | 0.50 | 87 |
| T + A | 0.25 | 1.00 | 87 |
| T + A | 0.25 | 2.00 | 76 |

EXAMPLE 38

Evaluation of test compounds as safeners for corn injury from postemergence applications of 5-ethyl-2 -(4-isopropyl-4-methyl-5-oxo-2-imidazolin-2-yl)nicotinic acid Corn plants (Pioneer 3475) in the third leaf stage are sprayed with a solution of 5-ethyl-2-(4-isopropyl- 4-methyl-5-oxo-2-imidazolin-2-yl)nicotinic acid, or a solution of 5-ethyl-2-(4-isopropyl-4-methyl-5 -oxo-2-imidazolin-2-yl)nicotinic acid mixed with a solution of a test compound. The 5-ethyl-2-(4-isopropyl- 4-methyl-5-oxo-2-imidazolin-2-yl)nicotinic acid and test compound solutions are diluted with water to provide the equivalent of 0.05 kg/ha of 5-ethyl-2-(4 -isopropyl-4-methyl-5-oxo-2-imidazolin-2-yl)nicotinic acid and 0.032 to 0.50 kg/ha of test compound to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 3 to 4 weeks after treatment, the tests are terminated and each pot is examined and rated by measuring the height of the foliage. The test results are averaged and expressed as a percent growth reduction compared to an untreated check, as described in example 18.

The results are summarized in Tables XXI and XXII. The tests reported in Table XXI are terminated 27 days after treatment and the tests reported in Table XXII are terminated 26 days after treatment.

In Tables XXI and XXII
A is 5-ethyl-2-(4-isopropyl-4-methyl-5-oxo-2 -imidazolin-2-yl)nicotinic acid;
B is the diammonium salt of 4-carboxy-3,4-dihydro-2H-1-benzopyran-4-acetic acid;
C is 4-carboxy-3,4-dihydro-2H-1-benzopyran-4-acetic acid;
D is 4-carboxy-6-chloro-3,4-dihydro-2H-1-benzopyran-4-acetate, diethyl ester;
E is 4-carboxy-6-chloro-3,4-dihydro-2H-1-benzopyran-4 -acetic acid;
F is 4-carboxy-8-chloro-3,4-dihydro-2H-1-benzopyran-4 -acetic acid;

G is 4-carboxy-6,8-dichloro-3,4-dihydro-2H-1-benzopyran-4-acetic acid;
H is 4-carboxy-6-chloro-3,4-dihydro-2H-1-benzothiopyran-4-acetic acid;
I is 4-carboxy-3,4-dihydro-2H-1-benzothiopyran-4-acetic acid;
J is 4-carboxy-6-fluoro-3,4-dihydro-2H-1-benzopyran-4-acetic acid;
K is 4-carboxy-6-fluoro-3,4-dihydro-2-methyl-2H-1-benzopyran-4-acetic acid, mixture of diastereomers;
L is 6-bromo-4-carboxy-3,4-dihydro-2H-1-benzopyran-4-acetic acid;
M is 7-bromo-4-carboxy-3,4-dihydro-2H-1-benzopyran-4-acetic acid;
N is 8-bromo-4-carboxy-3,4-dihydro-2H-1-benzopyran-4-acetic acid;
O is 4-carboxy-6,8-dibromo-3,4-dihydro-2H-1-benzopyran-4-acetic acid;
P is 4-carboxy-6-[(2-chloro-α,α,α,6-tetrafluoro-p-tolyl)oxy]-3,4-dihydro-2H-1-benzopyran-4-acetic acid;
Q is 4-carboxy-3,4-dihydro-6-methoxy-2H-1-benzopyran-4-acetic acid;
R is 4-carboxy-6,8-dimethyl-3,4-dihydro-2H-1-benzopyran-4-acetic acid; and
S is 2,2',3,3',4',5'-hexahydrospiro[2H-1-benzopyran-4,3'(2'H)-furan]-2',5'-dione.

TABLE XXI

| Treatment | Rate (kg/ha) | % Growth Reduction |
|---|---|---|
| A | 0.05 | 49 |
| B + A | 0.032 + 0.05 | 27 |
| B + A | 0.063 + 0.05 | 22 |
| B + A | 0.125 + 0.05 | 18 |
| B + A | 0.25 + 0.05 | 16 |
| B + A | 0.50 + 0.05 | 17 |
| C + A | 0.032 + 0.05 | 26 |
| C + A | 0.063 + 0.05 | 19 |
| C + A | 0.125 + 0.05 | 19 |
| C + A | 0.25 + 0.05 | 17 |
| C + A | 0.50 + 0.05 | 13 |
| D + A | 0.032 + 0.05 | 19 |
| D + A | 0.063 + 0.05 | 47 |
| D + A | 0.125 + 0.05 | 36 |
| D + A | 0.25 + 0.05 | 38 |
| D + A | 0.50 + 0.05 | 36 |
| E + A | 0.032 + 0.05 | 10 |
| E + A | 0.063 + 0.05 | 26 |
| E + A | 0.125 + 0.05 | 26 |
| E + A | 0.25 + 0.05 | 13 |
| E + A | 0.50 + 0.05 | 8 |
| F + A | 0.032 + 0.05 | 42 |
| F + A | 0.063 + 0.05 | 31 |
| F + A | 0.125 + 0.05 | 26 |
| F + A | 0.25 + 0.05 | 21 |
| F + A | 0.50 + 0.05 | 17 |
| G + A | 0.032 + 0.05 | 38 |
| G + A | 0.063 + 0.05 | 16 |
| G + A | 0.125 + 0.05 | 17 |
| G + A | 0.25 + 0.05 | 23 |
| G + A | 0.50 + 0.05 | 12 |
| H + A | 0.032 + 0.05 | 50 |
| H + A | 0.063 + 0.05 | 39 |
| H + A | 0.125 + 0.05 | 37 |
| H + A | 0.25 + 0.05 | 31 |
| H + A | 0.50 + 0.05 | 13 |
| I + A | 0.032 + 0.05 | 56 |
| I + A | 0.063 + 0.05 | 38 |
| I + A | 0.125 + 0.05 | 21 |
| I + A | 0.25 + 0.05 | 9 |
| I + A | 0.50 + 0.05 | 5 |
| J + A | 0.032 + 0.05 | 35 |
| J + A | 0.063 + 0.05 | 13 |
| J + A | 0.125 + 0.05 | 8 |
| J + A | 0.25 + 0.05 | 22 |

TABLE XXI-continued

| Treatment | Rate (kg/ha) | % Growth Reduction |
|---|---|---|
| J + A | 0.50 + 0.05 | 11 |
| K + A | 0.032 + 0.05 | 46 |
| K + A | 0.063 + 0.05 | 51 |
| K + A | 0.125 + 0.05 | 46 |
| K + A | 0.25 + 0.05 | 15 |
| K + A | 0.50 + 0.05 | 26 |

TABLE XXII

| Treatment | Rate (kg/ha) | % Growth Reduction |
|---|---|---|
| A | 0.05 | 33 |
| B + A | 0.032 + 0.05 | 22 |
| B + A | 0.063 + 0.05 | 17 |
| B + A | 0.125 + 0.05 | 23 |
| B + A | 0.25 + 0.05 | 20 |
| B + A | 0.50 + 0.05 | 20 |
| C + A | 0.032 + 0.05 | 19 |
| C + A | 0.063 + 0.05 | 19 |
| C + A | 0.125 + 0.05 | 18 |
| C + A | 0.25 + 0.05 | 12 |
| C + A | 0.50 + 0.05 | 4 |
| L + A | 0.032 + 0.05 | 27 |
| L + A | 0.063 + 0.05 | 29 |
| L + A | 0.125 + 0.05 | 25 |
| L + A | 0.25 + 0.05 | 23 |
| L + A | 0.50 + 0.05 | 18 |
| M + A | 0.032 + 0.05 | 56 |
| M + A | 0.063 + 0.05 | 48 |
| M + A | 0.125 + 0.05 | 26 |
| M + A | 0.25 + 0.05 | 11 |
| M + A | 0.50 + 0.05 | 16 |
| N + A | 0.032 + 0.05 | 46 |
| N + A | 0.063 + 0.05 | 37 |
| N + A | 0.125 + 0.05 | 32 |
| N + A | 0.25 + 0.05 | 21 |
| N + A | 0.50 + 0.05 | 17 |
| O + A | 0.032 + 0.05 | 27 |
| O + A | 0.063 + 0.05 | 25 |
| O + A | 0.125 + 0.05 | 45 |
| O + A | 0.2550 + 0.05 | 15 |
| O + A | 0.50 + 0.05 | 14 |
| P + A | 0.032 + 0.05 | 39 |
| P + A | 0.063 + 0.05 | 44 |
| P + A | 0.125 + 0.05 | 32 |
| P + A | 0.25 + 0.05 | 52 |
| P + A | 0.50 + 0.05 | 41 |
| Q + A | 0.032 + 0.05 | 39 |
| Q + A | 0.063 + 0.05 | 55 |
| Q + A | 0.125 + 0.05 | 22 |
| Q + A | 0.25 + 0.05 | 18 |
| Q + A | 0.50 + 0.05 | 20 |
| R + A | 0.032 + 0.05 | 37 |
| R + A | 0.063 + 0.05 | 49 |
| R + A | 0.125 + 0.05 | 34 |
| R + A | 0.25 + 0.05 | 59 |
| R + A | 0.50 + 0.05 | 16 |
| S + A | 0.032 + 0.05 | 47 |
| S + A | 0.063 + 0.05 | 18 |
| S + A | 0.125 + 0.05 | 27 |
| S + A | 0.25 + 0.05 | 12 |
| S + A | 0.50 + 0.05 | 9 |

EXAMPLE 39

Evaluation of 1-carboxy-1,2,3,4-tetrahydro-1-naphthaleneacetic acid as a safener for corn injury from postemergence applications of 5-ethyl-2-(4-isopropyl-4-methyl-5-oxo-2-imidazolin-2-yl)nicotinic acid Corn plants (Pioneer 3475) in the third leaf stage are sprayed with a solution of 5-ethyl-2-(4-isopropyl- 4-methyl- 5-oxo-2-imidazolin-2-yl)nicotinic acid, or a solution of 5-ethyl-2-(4-isopropyl-4-methyl-5-oxo-2-imidazolin-2-yl)nicotinic acid mixed with a solution of 1-carboxy-1,2,3,4-tetrahydro-1-naphthaleneacetic acid. The 5-ethyl-2-(4-isopropyl-4-methyl-5-oxo-2-imidazolin-2-yl)nicotinic acid and 1-carboxy-1,2,3,4-tetrahydro-1-naphthaleneacetic acid solutions are diluted with water to provide the equivalent of 0.05 kg/ha of 5-ethyl-2-(4-isopropyl-4-methyl-5-oxo-2-imidazolin-2-yl)nicotinic acid and 0.032 to 0.50 kg/ha of 1-carboxy-1,2,3,4-tetrahydro-1-naphthaleneacetic acid to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. Thirty days after treatment, the tests are terminated and each pot is examined and rated by measuring the height of the foliage. The test results are averaged and expressed as a percent growth reduction compared to an untreated check, as described in example 18.

The results are summarized in Table XXIII wherein
A is 5-ethyl-2-(4-isopropyl-4-methyl-5-oxo-2-imidazolin-2-yl)nicotinic acid; and
T is 1-carboxy-1,2,3,4-tetrahydro-1-naphthaleneacetic acid.

TABLE XXIII

| Treatment | Rate (kg/ha) | % Growth Reduction |
|---|---|---|
| A | 0.05 | 37 |
| T + A | 0.032 + 0.05 | 75 |
| T + A | 0.063 + 0.05 | 79 |
| T + A | 0.125 + 0.05 | 73 |
| T + A | 0.25 + 0.05 | 44 |
| T + A | 0.50 + 0.05 | 31 |

We claim:
1. A compound having the structural formula

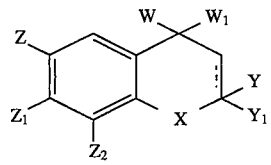

wherein
X is O or $S(O)_q$;
q is an integer of 0, 1 or 2;
Z, $Z_1$ and $Z_2$ are each independently hydrogen, F, Cl, Br, $C_1$–$C_4$ alkoxy, phenoxy optionally substituted with one or more halogen atoms or $C_1$–$C_4$ alkyl groups optionally substituted with one or more halogen atoms, or $C_1$–$C_4$ alkyl optionally substituted with one or more halogen atoms, $C_1$–$C_4$ alkoxy groups or hydroxy groups, provided that only one of Z—$Z_2$ is $C_1$–$C_3$ alkoxyalkyl or phenoxy optionally substituted with one or more halogen atoms or $C_1$–$C_4$ alkyl groups optionally substituted with one or more halogen atoms;

Y and $Y_1$ are each independently hydrogen, F, Cl or $C_1$–$C_3$ alkyl, provided that when Y is F or Cl, then $Y_1$ is hydrogen;
W is $CH_2A$ or when taken together with $W_1$, $WW_1$ is represented by the structure —$CH_2C(O)OC(O)$—;
$W_1$ is A or when taken together with W, $W_1W$ is represented by the structure —$C(O)OC(O)CH_2$—;
A is $C(O)X_1$ or $CH(OR_4)_2$;
$X_1$ is $OR_5$ or $SR_9$;
$R_5$ is hydrogen, $C_1$–$C_6$ alkyl, $C_3$–$C_6$ alkenyl, $C_3$–$C_6$ alkynyl or an alkali metal, alkaline earth metal, manganese, copper, zinc, cobalt, silver, nickel, ammonium or organic ammonium cation;
$R_9$ is hydrogen, $C_1$–$C_6$ alkyl, $C_3$–$C_6$ alkenyl or $C_3$–$C_6$ alkynyl;
$R_4$ is $C_1$–$C_6$ alkyl and when taken together $R_4$ and a second $R_4$ may form a ring in which $R_4R_4$ are represented by —$(CH_2)_2$— or —$(CH_2)_3$—; and the optical isomers thereof;
provided that when Y is hydrogen and $Y_1$ is hydrogen or $C_1$–$C_3$ alkyl, then one of Z, $Z_1$ or $Z_2$ is phenoxy optionally substituted with one or more halogen atoms or $C_1$–$C_4$ alkyl groups optionally substituted with one or more halogen atoms.

2. The compound according to claim 1 wherein
X is O or S;
Z is phenoxy optionally substituted with one or more halogen atoms or $C_1$–$C_4$ alkyl groups optionally substituted with one or more halogen atoms;
$Z_1$ and $Z_2$ are each independently hydrogen, F, Cl, Br or $C_1$–$C_4$ alkyl optionally substituted with one or more halogen atoms, $C_1$–$C_4$ alkoxy groups or hydroxy groups;
Y and $Y_1$ are each independently hydrogen or $C_1$–$C_3$ alkyl;
W is $CH_2C(O)OR_5$;
$W_1$ is $C(O)OR_5$; and
$R_5$ is hydrogen, $C_1$–$C_6$ alkyl or an alkali metal, alkaline earth metal, ammonium or organic ammonium cation.

3. The compound according to claim 2 wherein
X is O;
Z is phenoxy optionally substituted with one or more halogen atoms or $C_1$–$C_4$ alkyl groups optionally substituted with one or more halogen atoms;
$Z_1$ and $Z_2$ are each independently hydrogen, F, Cl or Br;
Y and $Y_1$ are each independently hydrogen;
W is $CH_2C(O)OR_5$;
$W_1$ is $C(O)OR_5$; and
$R_5$ is hydrogen, $C_1$–$C_6$ alkyl or an alkali metal, alkaline earth metal, ammonium or organic ammonium cation.

4. The compound according to claim 3 4-carboxy-6-[(2-chloro-α,α,α,6-tetrafluoro-p-tolyl)oxy]-3,4-dihydro-2H-1-benzopyran-4-acetic acid.

* * * * *